(12) United States Patent
Miller et al.

(10) Patent No.: US 7,541,150 B2
(45) Date of Patent: Jun. 2, 2009

(54) METHOD FOR THE DIAGNOSIS AND PROGNOSIS OF MALIGNANT DISEASES

(75) Inventors: Donald M. Miller, Louisville, KY (US); Paula J. Bates, Louisville, KY (US); John O. Trent, Louisville, KY (US); Xiaohua Xu, Louisville, KY (US)

(73) Assignee: University of Louisville Research Foundation, Inc, Louisville, KY (US)

( * ) Notice: Subject to any disclaimer, the term of this patent is extended or adjusted under 35 U.S.C. 154(b) by 982 days.

(21) Appl. No.: 10/118,854

(22) Filed: Apr. 8, 2002

(65) Prior Publication Data

US 2003/0194754 A1   Oct. 16, 2003

(51) Int. Cl.
*G01N 33/53* (2006.01)
(52) U.S. Cl. ...................................... 435/7.1
(58) Field of Classification Search .................. 436/64, 436/500; 435/7.1
See application file for complete search history.

(56) References Cited

U.S. PATENT DOCUMENTS

| | | | |
|---|---|---|---|
| 4,474,892 A | 10/1984 | Murad et al. | |
| 4,522,811 A | 6/1985 | Eppstein et al. | |
| 4,665,897 A | 5/1987 | Lemelson | |
| 5,093,246 A | 3/1992 | Cech et al. | |
| 5,192,660 A | 3/1993 | Reed-Gitomer | |
| 5,545,807 A | 8/1996 | Surani et al. | |
| 5,567,595 A | 10/1996 | Kok | |
| 5,629,197 A | 5/1997 | Ring et al. | |
| 5,736,348 A | 4/1998 | Goldenberg et al. | |
| 5,770,429 A | 6/1998 | Lonberg et al. | |
| 5,925,334 A | 7/1999 | Rubin et al. | 424/45 |
| 5,932,475 A | 8/1999 | Bandman et al. | 435/320.1 |
| 6,048,703 A | 4/2000 | Siman et al. | |
| 6,096,532 A | 8/2000 | Armstrong et al. | |
| 6,291,643 B1 | 9/2001 | Zou et al. | |
| 6,306,404 B1 | 10/2001 | LaPosta et al. | |
| 6,325,785 B1 | 12/2001 | Babkes et al. | 604/319 |
| 6,339,075 B1 | 1/2002 | King et al. | 514/59 |
| 6,350,452 B1 | 2/2002 | Riss | |
| 6,462,189 B1 | 10/2002 | Koide | |
| 6,506,559 B1 | 1/2003 | Fire et al. | |
| 2002/0028488 A1 | 3/2002 | Singh et al. | |
| 2004/0132049 A1 | 7/2004 | Bates et al. | |
| 2005/0053607 A1 | 3/2005 | Bates et al. | |

FOREIGN PATENT DOCUMENTS

| | | |
|---|---|---|
| DE | 10037861 | 2/2002 |
| JP | 07 242566 A | 9/1995 |
| WO | WO 95/20401 | 8/1995 |
| WO | WO 97/22250 | 6/1997 |
| WO | WO 98/24893 | 6/1998 |
| WO | WO 98/40480 | 9/1998 |
| WO | WO 9840480 A1 * | 9/1998 |
| WO | WO 99/06588 | 2/1999 |
| WO | WO00/61597 | 10/2000 |
| WO | WO 00/61597 | 10/2000 |
| WO | WO 00/63250 | 10/2000 |
| WO | WO 01/32832 | 5/2001 |
| WO | WO 01/35093 | 5/2001 |
| WO | WO 01/68836 | 9/2001 |
| WO | WO 01/75164 | 10/2001 |
| WO | WO 01/91787 | 12/2001 |
| WO | WO 02/12437 | 2/2002 |
| WO | WO 02/44231 | 6/2002 |
| WO | WO 03/029277 | 4/2003 |
| WO | WO 03/005617 | 10/2003 |
| WO | WO03/086174 | 10/2003 |
| WO | WO 03/086174 | 10/2003 |
| WO | WO03/087124 | 10/2003 |
| WO | WO 03/087124 | 10/2003 |
| WO | WO 2004/003554 | 1/2004 |
| WO | WO 2005/035579 | 4/2005 |

OTHER PUBLICATIONS

Haese A (Urologe A Sep. 2003;42(9):1172-1187—Abstract Only.*
Mikolajczyk et al Rinsho Byori. Mar. 2004; 52(3):223-30.*
Nonomura et al (Surg Today 1993:23(6):486-490).*
Kennedy et al (Chest 2000;117(Suppl 1):72S-79S).*
Harms et al (Biochem J. 2001; 360:531-538).*
http://www.abcam.com/?datasheet=7898.*
Nature Reviews Dec. 2000; 1:233-236.*
Bates, P.J., J.B. Kahlon, S.D. Thomas, JO. Trent et al 1999 Antiprohferative activity of G-rich oligonucleotides correlates with protein binding. $JBE_ol$ Chem. 274:26369-77.
Callebaut, C., J. Blanco, N. Benkirane, B. Krust, et al 1998. Identification of V3 loop-binding proteins as potential receptors implicated in the binding of HIV particles to CD4(+) cells. JBiol Chem. 273:21988-97.
Carney, D.N., A.F. Gazdar, U. Bepler, J.G. Guccion, et al 1985. Establishment and 10 identification of small cell lung cancer cell lines having classic and variant features. Cancer Res. 45:2913-23.
Davis, K.A., Y. Lin, B. Abrams, and S.D. Jayasena. 1998. Staining of cell surface human CD4 with 2'-F-pyrimidine-containing RNA aptamers for flow cytometry. Nucleic Acids Res. 26:3915-24.
Derenzini, M. 2000. The AgNORs. Micron. 3 1:117-20.
Gey, G., W. Coffman, and M. Kubicek. 1952. Tissue culture studies of the proliferative capacity of cervical carcinoma and normal epithelium. Cancer Res. 12:264.
Giaccone, U., J. Battey, A.F. Gazdar, H. Oie, et al 1992. Neuromedin B is present in 20 lung cancer cell lines. Cancer Res. 52:2732s-2736s.
Ginisty, H., H. Sicard, B. Roger, and P. Bouvet. 1999. Structure and functions of nucleolin. J Cell SeE. 112:761-72.
Kim, CS., B.B. Berkley, W.M. Abraham, and A. Wanner. 1982. A micro double capillary method for rheologic measurements of lower airway secretions. Bull Eur Physiopathol Respir. 18:915-27.
Langer, P.R., A.A. Waldrop, and D.C. Ward. 1981. Enzymatic synthesis of biotinlabeled polynucleotides: novel nucleic acid affinity probes. Proc Natl Acad Sci USA. 78:6633-7.

(Continued)

Primary Examiner—Christopher H Yaen
(74) Attorney, Agent, or Firm—Evan Law Group LLC

(57) ABSTRACT

Methods for the diagnosis of cancer by determining the neoplastic status of a cell by probing the cell plasma membrane for the presence of nucleolin are provided, as are kits to carry out such tests.

34 Claims, 4 Drawing Sheets

OTHER PUBLICATIONS

Lin, D.L., and C. Chang. 1996. p53 is a mediator for radiation-repressed human 1R2 orphan receptor expression in MCF-7 cells, a new pathway from tumor suppressor to member of the steroid receptor superfamily. $JBI_o1$ Chem. 271: 14649-52.

Little, CD., M.M. Nau, D.N. Carney, A.F. Gazdar, et at 1983. Amplification and expression of the c-myc oncogene in human lung cancer cell lines. Nature. 306:194-6.

McNicol, AM., and J.A. Richmond. 1998. Optimizing immunohistochemistry: antigen retrieval and signal amplification. Histopathology. 32:97-103.

Mickey, D.D., KR. Stone, H. Wunderli, G.H. Mickey, et at 1977. Heterotransplantation of a human prostatic adenocarcinoma cell line in nude mice. Cancer Res. 37:4049-58.

Naito, M., H. Hamada, and T. Tsuruo. 1988. AIP/Mg -dependent binding of vincristine to the plasma membrane of multidrug-resistant K562 cells. JBIol Chem. 263:11887-91.

Orfao, A., and A Ruiz-Arguelles. 1996. General concepts about cell sorting techniques. GlEn Biochem 29:5-9.

Robinson, J.M., and D.D. Vandre. 2001. Antigen retrieval in cells and tissues: enhancement with sodium dodecyl sulfate. Histochern CellBiol. 116:119-30.

Shi, SR., R.J. Cote, and CR. Taylor. 1997. Antigen retrieval immunohistochemistry: past, present, and future. JHistochem Cytochem. 45:327-43.

Shi, S.R., R.J. Cote, and CR. Taylor. 2001. Antigen retrieval techniques: current perspectives. JHistochenz Cytochem. 49:931-7.

Sorokina, E.A., and JO. Kleinman. 1999. Cloning and preliminary characterization of a calcium-binding protein closely related to nucleolin on the apical surface of inner medullary collecting duct cells. J Biol Chern. 274:27491-6.

Srivastava, M., and H.B. Pollard. 1999. Molecular dissection of nucleolin's role in growth and cell proliferation: new insights. FasebJ. 13:1911-22.

Stone, K.R., D.D. Mickey, H. Wunderli, G.H. Mickey, et at 1978. Isolation of a human prostate carcinoma cell line (DU 145). Int J Cancer. 21:274-81.

Takahashi, T., M.M. Nau, I. Chiba, Mi. Birrer, et at 1989. p53: a frequent target for genetic abnormalities in lung cancer. Science. 246:491-4.

Tockman, MS., J.L. Mulshine, S. Piantadosi, Y.S. Erozan, et at 1997. Prospective detection of preclinical lung cancer: results from two studies of heterogeneous nuclear ribonucleoprotein A2/B1 overexpression. Clin Cancer Res. 3:2237-46.

Tuteja, R., and N. Tuteja. 1998. Nucleolin: a multifunctional major nucleolar phosphoprotein. Grit Rev Biocheni Mol Biol. 33:407-36.

van de Loosdrecht, A.A., R.H. Beelen, G.J. Ossenkoppele, MG Broekhoven, et at 1994. A tetrazolium-based colorimetric MTI assay to quantitate human monocyte mediated cytotoxicity against leukemic cells from cell lines and patients with acute myeloid leukemia. Jmmnzunol Methods. 174:311-20.

Wysocki, L.J., and V.L. Sato. 1978. "Panning" for lymphocytes: a method for cell selection. Proc Natl Acad Sd US A. 75:2844-8.

Xu, X., F. Hamhouyia, S.D. Thomas, T.J. Burke, et at 2001. Inhibition of DNA Replication and Induction of S Phase Cell Cycle Arrest by 0-rich Oligonucleotides. JBiol Chem. 276:43221-30.

Yao, G.Q., S. Corrias, and Y.C. Cheng. 1996a. Identification of two oligodeoxyribonucleotide binding proteins on plasma membranes of human cell lines. Biochern Pharmacol. 51:431-6.

Ballou, B., et al., "Three-Dimensional Imaging of Nucleolin Traffocking in Normal Cells, Transfectants, and Heterokaryons", 1996, SPIE, vol. 2680, pp. 124-131.

Ballou, B., et al., "Tumor Detection and Visualization Using Cyanine Fluorochrome-Labeled Antibodies", 1997, Biotechnol. Prog., 13, pp. 649-658.

Ballou, B., et al., "Tumor Labeling in Vivo Using Cyanine-Conjugated Monoclonal Antibodies", 1995, Cancer Immunol Immunother 41, pp. 257-263.

Ballou, B., et al., Abstract of Cyanine Fluorocrome-Labeled Antibodies In Vivo: Assessment of Tumor Imaging Using Cy3, Cy5, Cy5.5, and Cy7., 1998, Cancer Detect Prev. 22(3), pp. 251-257.

Hovanessian, et al., The Cell-Surface-Expressed Nucleolin Is Associated With The Actin Cytoskeleton, Experimental Cell Research, (2000), 261:312-328.

Semenkovich, et al., A Protein Expressed on the Surface of HepG2 Cells That Binds Lipoproteins Specifically is Nucleolin, Biochemistry, (1990), 29:9708-9713.

European Search Report for a corresponding Application No. 03728350.4 Dated Jul. 12, 2005.

Bates, P.J., et al., "Antiproliferative Activity of G-rich Oligonucleotides Correlates with Protein Binding"., Journal of Biological Chemistry, vol. 274, No. 37, pp. 26369-26377, (1999).

Kwiatkowski, B.A., et al., "Identification and cloning of a novel chromatin-associated protein partner of Epstein-Barr nuclear protein 2"., Experimental Cell Research, vol. 300, No. 1, pp. 223-233, (2004).

Abstract of: Mi, Y., et al., "Validation of nucleolin as a novel target for cancer drug discovery"., Proceedings of the annual meeting of the American Association for Cancer Research, vol. 43, pp. 959-960, (2002).

Schade et al., "The Production of Avian (Egg Yolk) Antibodies IgY. The Report and Recommendations of ECVAM Workshop," Alternatives to Laboratory Animals (ATLA), 1996, pp. 925-934, vol. 24.

Abaza, M.S.I, et al, "Effects of amino acid substitutions outside an antigenic site on protein binding to monoclonal antibodies of predetermined specificity obtained by peptide immunization: Demonstration with region 94-100 (antigenic site 3) of myoglobin", Journal of Protein Chemistry, vol. 11, No. 5, pp. 433-444, (1992).

Aihara, M, et al, "The frequency of apoptosis correlates with the prognosis of Gleason Grade 3 adenocarcinoma of the prostate", Cancer, vol. 75, No. 2, pp. 522-529, (1995).

Ali, S, et al, "Absorption, distribution, metabolism, and excretion of a respirable antisense oligonucleotide for asthma", Am J Respir Crit Care Med, vol. 163, No. 4, pp. 989-993, (2001).

Alvarex-Gonzalez, R, et al, "Selective loss of poly(ADP-ribose) and the 85-kDa fragment of ply(ADP-ribose) polymerase in nucleoli during alkylation-induced apoptosis of HeLa Cells", J Biol Chem., vol. 274, No. 45, pp. 32122-32126, (1999).

Anderson, H.J, et al, "Flow cytometry of mitotic cells", Exp Cell Research, vol. 238, No. 2, pp. 498-502, (1998).

Ballou, B, et al, "Three-Dimensional Imaging of Nucleolin Traffocking in Normal Cells, Transfectants, and Heterokaryons", SPIE, vol. 2680, pp. 124-131, (1996).

Ballou, B, et al, "Tumor Detection and Visualization Using Cyanine Fluorochrome-Labeled Antibodies", Biotechnol Prog, vol. 13, pp. 649-658, (1997).

Ballou, B, et al, "Tumor Labeling in Vivo Using Cyanine-Conjugated Monoclonal Antibodies", Cancer Immunol Immunother, vol. 41, pp. 257-263, (1995).

Ballou, B, et al, Abstract of "Cyanine Fluorocrome-Labeled Antibodies In Vivo: Assessment of Tumor Imaging Using Cy3, Cy5, Cy5.5, and Cy7", Cancer Detect Prev, vol. 22, No. 3, pp. 251-257, (1998).

Baran, N, et al, "The SV40 large T-antigen helicase can unwind four stranded DNA structures linked by G-quartets", Nucleic Acids Research, vol. 25, No. 2, pp. 297-303, (1997).

Bates, P.J, et al, "Antiproliferative activity of G-rich oligonucleotides correlates with protein binding", The Journal of Biological Chemistry, vol. 274, No. 37, pp. 26369-26377, (1999).

Beltinger, C, et al, "Binding, uptake, and intracellular trafficking of phosphorothioate-modified oligodeoxynucleotides", J Clin Invest, vol. 95, No. 4, pp. 1814-1823, (1995).

Benimetskaya, L, et al, "Formation of a G-tetrad and higher order structures correlates with biological activity of the Re1A (NF-kappaB p65) 'antisense' oligodeoxynucleotide", Nucleic Acids Research, vol. 25, No. 13, pp. 2648-2656, (1997).

Benton, B.M, et al, "A novel FK506- and rapamycin-binding protein (FPR3 gene product) in the yeast Saccharomyces cerevisiae is a praline rotamase localized to the nucleolus", J Cell Biol, vol. 127, No. 3, pp. 623-639, (1994).

Bergsmedh, A, et al, "Loss of the p21(Cip1/Waf1) cyclin kinase inhibitor results in propagation of horizontally transferred DNA", Cancer Research, vol. 62, No. 2, pp. 575-579, (2002).

Bernstein, E, et al, "Role for a bidentate ribonuclease in the initiation step of RNA interference", Nature, vol. 409, No. 6818, pp. 363-366, (2001).

Bharti, A.K, et al, "Identification of a nucleolin binding site in human topoisomerase I", J Biol Chem, vol. 271, No. 4, pp. 1993-1997, (1996).

Biggiogera, M, et al, "Heterogeneous ectopic RNP-derived structures (HERDS) are markers of transcriptional arrest", FASEB J, vol. 14, No. 5, pp. 828-834, (2000).

Biscotti, C.V, et al, "Apoptotic bodies: a consistent morphologic feature of endocervical adenocarcinoma in situ", American Journal of Surgical Pathology, vol. 22, No. 4, pp. 434-439, (1998).

Bishop, J.S, et al, "Intramolecular G-quartet motifs confer nuclease resistance to a potent anti-HIV oligonucleotide", J Biol Chem, vol. 271, No. 10, pp. 5698-5703, (1996).

Bock, L.C, et al, "Selection of single-stranded DNA molecules that bind and inhibit human thrombin", Nature, vol. 355, No. 6360, pp. 564-566, (1992).

Borggrefe, T, et al, "A B-cell-specific DNA recombination complex", J Biol Chem, vol. 273, No. 27, pp. 17025-17035, (1998).

Bortul, R, et al, "Nuclear changes in necrotic HL-60 cells", J Cell Biochem, vol. 81, No. S36, pp. 19-31, (2001).

Boulares, A.H, et al, "Role of poly(ADP-ribose) polymerase (PARP) cleavage in apoptosis. Caspase 3-resistant PARP mutant increases rates of apoptosis in transfected cells", Journal of Biochemical Chemistry, vol. 274, No. 33, pp. 22932-22940, (1999).

Boulares, A.H, et al, "Roles of DNA fragmentation factor and poly(ADP-ribose) polymerase in an amplification phase of tumor necrosis factor-induced apoptosis", Journal of Biological Chemistry, vol. 276, No. 41, pp. 38185-38192, (2001).

Brockstedt, E, et al, "Identification of apoptosis-associated proteins in a human Burkitt lymphoma cell line. Cleavage of heterogeneous nuclear ribonucleoprotein A1 by caspase 3", J Biol Chem, vol. 273, No. 43, pp. 28057-28064, (1998).

Buys, C.H, "Telomeres, telomerase, and cancer", N Engl J Med, vol. 342, No. 17, pp. 1282-1283, (2000).

Callebaut, C, et al, "Identification of V3 loop-binding proteins as potential receptors implicated in the binding of HIV particles to CD4(+) cells", J Biol Chem, vol. 273, No. 34, pp. 21988-21997, (1998).

Cannavo, G, et al, "Abnormal intracellular kinetics of cell-cycle-dependent proteins in lymphocytes from patients infected with human immunodeficiency virus: a novel biologic link between immune activation, accelerated t-cell turnover, and high levels of apoptosis", Blood, vol. 97, No. 6, pp. 1756-1764, (2001).

Carney, D.N, et al, "Establishment and identification of small cell lung cancer cell lines having classic and variant features", Cancer Research, vol. 45, pp. 2913-2923, (1985).

Carvalho, P.E, et al, "Useful prognostic panel markers to express the biological tumor status in resected lung adenocarcinomas", Jpn J Clin Oncol, vol. 30, No. 11, pp. 478-486, (2000).

Choi, N.G, et al, "Apoptosis and nuclear shapes in benign prostate hyperplasia and prostate adenocarcinoma: comparison with and relation to Gleason score", Int J Urol, vol. 6, No. 1, pp. 13-18, (1999).

Coqueret, O, et al, "Functional interaction of STAT3 transcription factor with the cell cycle inhibitor p21$^{WAF1/CIP1/SDI1}$", J Biol Chem, vol. 275, No. 25, pp. 18794-18800, (2000).

Cowan, K.H, et al, "Dihydrofolate reductase gene amplification and possible rearrangement in estrogen-responsive methotrexate-resistant human breast cancer cells", J Biol Chem, vol. 257, No. 24, pp. 15079-15086, (1982).

D'Amours, D, et al, "Poly(ADP-ribosyl)ation reactions in the regulation of nuclear functions", Biochem J, vol. 342, pt. 2, pp. 249-268, (1999).

Dapic, V, et al, "Antiproliferative activity of G-Quartet-forming oligonucleotides with backbone and sugar modifications", Biochemistry, vol. 41, No. 11, pp. 3676-3685, (2002).

David, K, et al, "Initial characterization of the apoptosis-inducing receptor for natural human anti-neuroblastoma IgM", Med Pediatr Oncol, vol. 36, No. 1, pp. 251-257, (2001).

David-Pfeuty, T, "Potent inhibitors of cyclin-dependent kinase 2 induce nuclear accumulation of wild-type p53 and nucleolar fragmentation in human untransformed and tumor-derived cells", Oncogene, vol. 18, No. 52, pp. 7409-7422, (1999).

Davis, K.A, et al, "Staining of cell surface human CD4 with 2'-F-pyrimidine-containing RNA aptamers for flow cytometry", Nucleic Acids Research, vol. 26, pp. 3915-3924, (1998).

De Jong, J.S, et al, "Number of apoptotic cells as a prognostic marker in invasive breast cancer", Br J Cancer, vol. 82, No. 2, pp. 368-373, (2000).

Dempsey, L.A, et al, "A specific isoform of hnRNP D interacts with DNA in the LR1 heterodimer: canonical RNA binding motifs in a sequence-specific duplex DNA binding protein", J Biol Chem, vol. 273, No. 44, pp. 29224-29229, (1998).

Dempsey, L.A, et al, "G4 DNA binding by LR1 and its subunits, nucleolin and hnRNP D, A role for G-G pairing in immunoglobulin switch recombination", J Biol Chem, vol. 274, No. 2, pp. 1066-1071, (1999).

Derenzini, M. "The AgNORs", Micron, vol. 31, No. 2, pp. 117-120, (2000).

Desnoyers, S, et al, "Alteration of the nucleolar localization of poly(ADP-ribose) polymerase upon treatment with transcription inhibitors", Exp Cell Research, vol. 227, No. 1, pp. 146-153, (1996).

Dickinson, L.A, et al, "Nucleolin is a matrix attachment region DNA-binding protein that specifically recognizes a region with base-unpairing potential", Mol Cell Biology, vol. 15, No. 1, pp. 456-465, (1995).

Dranovsky, A, et al, "Cdc2 phosphorylation of nucleolin demarcates mitotic stages and alzheimer's disease pathology", Neurobiol Aging, vol. 22, No. 4, pp. 517-528, (2001).

Drews, J, "Drug discovery: a historical perspective", Science, vol. 287, No. 5460, pp. 1960-1964, (2000).

Drews J, et al, "Classic drug targets (special pull-out)", Nature Biotechnology, vol. 15, (1997).

Dryden, S, et al, "The lack of specificity of neuropeptide Y (NPY) antisense oligodeoxynucleotides administered intracerebroventricularly in inhibiting food intake and NPY gene expression in the rat hypothalamus", J Endocrinol, vol. 157, No. 1, pp. 169-175, (1998).

Dumler, I, et al, "Urokinase-induced mitogenesis is mediated by casein kinase 2 and nucleolin", Curr Biol, vol. 9, No. 24, pp. 1468-1476, (1999).

Dundr, M, et al, "The dynamics of postmitotic reassembly of the nucleolus", J Cell Biol, vol. 150, No. 3, pp. 433-446, (2000).

Edwards, T.K, et al, "Role for nucleolin/Nsr1 in the cellular localization of topoisomerase I", J Biol Chem, vol. 275, No. 46, pp. 36181-36188, (2000).

Erard, M.S, et al, "A major nucleolar protein, nucleolin, induces chromatin decondensation by binding to histone H1", Eur J Biochem, vol. 175, No. 3, pp. 525-530, (1988).

European Search Report for Application No. 03728350.4 dated Jul. 12, 2005.

Facompre, M, et al, "Apoptotic response of HL-60 human leukemia cells to the antitumor drug NB-506, a glycosylated indolocarbazole inhibitor of topoisomerase 1", Biochem Pharmacol, vol. 61, No. 3, pp. 299-310, (2001).

Feltzer, R.E, et al, "Alkaline proteinase inhibitor of *Pseudomonas aeruginosa*. Interaction of native and N-terminally truncated inhibitor proteins with Pseudomonas metalloproteinases", J Biol Chem, vol. 275, No. 28, pp. 21002-21009, (2000).

Fry, M, et al, "Human Werner syndrome DNA helicase unwinds tetrahelical structures of the fragile X syndrome repeat sequence d(CGG)n", J Biol Chem, vol. 274, No. 18, pp. 12797-12802, (1999).

Gascoyne, R.D, et al, "Prognostic significance of Bcl-2 protein expression and Bcl-2 gene rearrangement in diffuse aggressive non-Hodgkin's lymphoma", Blood, vol. 90, No. 1, pp. 244-251, (1997).

Gautier, F, et al, "Production and characterisation of a monoclonal antibody specific for apoptotic bodies derived from several tumour cell lines", Journal of Immunological Methods, vol. 228, pp. 49-58, (1999).

Gavrieli, Y, et al, "Identification of programmed cell death in situ via specific labeling of nuclear DNA fragmentation", The Journal of Cell Biology, vol. 119, No. 3, pp. 493-501, (1992).

Gey, G, et al, "Tissue culture studies of the proliferative capacity of cervical carcinoma and normal epithelium", Cancer Research, vol. 12, pp. 264, (1952).

Ghosh, M, et al, "Apoptosis in squamous cell carcinoma of the lung: correlation with survival and clinicopathological features", J Clin Pathol, vol. 54, No. 2, pp. 111-115, (2001).

Giaccone, G, et al, "Neuromedin B is present in lung cancer cell lines", Cancer Research, vol. 52, pp. 2732s-2736s, (1992).

Gibbs, J.B, "Mechanism-based target identification and drug discovery in cancer research", Science, vol. 287, No. 5460, pp. 1969-1973, (2000).

Gil, D, et al, "Intracellular redistribution of nucleolin upon interaction with the CD3epsilon chain of the T cell receptor complex", J Biol Chem, vol. 276, No. 14, pp. 11174-11179, (2001).

Giles, R.V, et al, "Selecting optimal oligonucleotide composition for maximal antisense effect following streptolysin O-mediated delivery into human leukaemia cells", Nucleic Acids Research, vol. 26, No. 7, pp. 1567-1575, (1998).

Ginisty, H, et al, "Structure and functions of nucleolin", J Cell Science, vol. 112, Pt. 6, pp. 761-772, (1999).

Giraldo, R, et al, "The yeast telomere-binding protein RAP1 binds to and promotes the formation of DNA quadruplexes in telomeric DNA", EMBO J, vol. 13, No. 10, pp. 2411-2420, (1994).

Green, D.W, et al, "Beta-catenin antisense treatment decreases beta-catenin expression and tumor growth rate in colon carcinoma xenografts", J Surg Res, vol. 101, No. 1, pp. 16-20, (2001).

Grinstein, E, et al, "Nucleolin as Activator of Human Papillomavirus Type 18 Oncogene Transcription in Cervical Cancer", J Exp Med, vol. 196, No. 8, pp. 1067-1078, The Rockefeller University Press, (2002).

Gudas, J.M, et al, "Drug-resistant breast cancer cells frequently retain expression of a functional wild-type p53 protein", Carcinogenesis, vol. 17, No. 7, pp. 1417-1427, (1996).

Haese, A, "Serum markers for early detection and staging of prostate cancer, status report on current and future markers", Urologe A, vol. 42, No. 9, pp. 1172-1187, (2003.—(Abstract Only).

Halicka, H.D, et al, "Segregation of RNA and separate packaging of DNA and RNA in apoptotic bodies during apoptosis", Exp Cell Research, vol. 260, No. 2, pp. 248-256, (2000).

Hanakahi, L.A, et al, "High affinity interactions of nucleolin with G-G-paired rDNA", J Biol Chem, vol. 274, No. 22, pp. 15908-15912, (1999).

Harms, G, et al, "Identification of nucleolin as a new L-selectin ligand", Biochem J, vol. 360, pp. 531-538, (2001).

Herceg, Z, et al, "Failure of poly(ADP-ribose) polymerase cleavage by caspases leads to induction of necrosis and enhanced apoptosis", Mol Cell Biol, vol. 19, No. 7, pp. 5124-5133, (1999).

Hirata, D, et al, "Nucleolin as the earliest target molecule of autoantibodies produced in MRL/lpr lupus-prone mice", Clin Immunol, vol. 97, No. 1, pp. 50-58, (2000).

Holdenrieder, S, et al, "Nucleosomes in serum as a marker for cell death", Clin Chem Lab Med, vol. 39, No. 7, pp. 596-605, (2001).

Holdenrieder, S, et al, "Nucleosomes in serum of patients with benign and malignant diseases", Int. J. Cancer, vol. 95, pp. 114-120, (2001).

Holdenrieder, S, et al, "Circulating nucleosomes in serum", Annals New York Academy of Sciences, vol. 945, pp. 93-102, (2001).

Holdenrieder, S, et al, "Quantification of nucleosomes in serum by the cell death detection ELISAplus", Biochemica, No. 1, pp. 25-27, (2002), (http://www.roche-applied-science.com/biochemica/no1_02/PDF/p25.pdf).

Holmgren, L, et al, "Horizontal transfer of DNA by the uptake of apoptotic bodies", Blood, vol. 93, No. 11, pp. 3956-3963, (1999).

Horky, M, et al, "Segregation of nucleolar components coincides with caspase-3 activation in cisplatin-treated HeLa cells", J Cell Science, vol. 114, pt. 4, pp. 663-670, (2001).

Hovanessian, A.G, et al, "The cell-surface-expressed nucleolin is associated with the actin cytoskeleton", Experimental Cell Research, vol. 261, pp. 312-328, (2000).

Huang, Z, "Bcl-2 family proteins as targets for anticancer drug design", Oncogene, vol. 19, No. 56, pp. 6627-6631, (2000).

International Search Report dated Nov. 13, 2003 for PCT application No. PCT/US03/20167.

International Search Report dated Aug. 3, 2004 for PCT application No. PCT/US03/10745.

International Search Report dated Mar. 14, 2005 for PCT application No. PCT/US04/033174.

Irving, R.A, et al, "Ribosome display and affinity maturation: from antibodies to single v-domains and steps towards cancer therapeutics", J Immunol Methods, vol. 248, issues 1-2, pp. 31-45, (2001).

Jordan, P, et al, "Major cell surface-located protein substrates of an ecto-protein kinase are homologs of known nuclear proteins", Biochemistry, vol. 33, No. 49, pp. 14696-14706, (1994).

Jungblut, P.R, et al, "Proteomics in human disease: cancer, heart and infectious diseases", Electrophoresis, vol. 20, No. 10, pp. 2100-2110, (1999).

Kennedy, T.C, et al, "Screening for lung cancer revisited and the role of sputum cytology and fluorescence bronchoscopy in a high-risk group", Chest, vol. 117, supplemental 4, pp. 72S-79S, (2000).

Kerr, J.F, et al, "Apoptosis: a basic biological phenomenon with wide-ranging implications in tissue kinetics", Br J Cancer, vol. 26, pp, 239-257, (1972).

Kim, C.S, et al, "A micro double capillary method for rheologic measurements of lower airway secretions", Bull Eur Physiopathol Respir, vol. 18, pp. 915-927, (1982).

Kuby, J, "Antigens", Immunology, Second Edition, chapter 4, pp. 85-96, W.H. Freeman and Company, New York, (1994).

Kwiatkowski, B.A, et al, "Identification and cloning of a novel chromatin-associated protein partner of Epstein-Barr nuclear protein 2", Experimental Cell Research, vol. 300, pp. 223-233, (2004).

Langer, P.R, et al, "Enzymatic synthesis of biotin-labeled polynucleotides: novel nucleic acid affinity probes", Proc Natl Acad Sci USA, vol. 78, pp. 6633-6637, (1981).

Larrucea, S, et al, "Cellular adhesion mediated by factor J, a complement inhibitor. Evidence for nucleolin involvement", J Biol Chem, vol. 273, No. 48, pp. 31718-31725, (1998).

Lau, Q.C, et al, "In vivo pro-apoptotic and antitumor efficacy of a c-Raf antisense phosphorothioate oligonucleotide: relationship to tumor size", Antisense Nucleic Acid Drug Development, vol. 12, No. 1, pp. 11-20, (2002).

Leitinger, N, et al, "ADP-ribosylation of nucleolar proteins in HeLa tumor cells", J Cell Biochem, vol. 52, No. 2, pp. 153-158, (1993).

Lichtenstein, A.V, et al, "Circulating nucleic acids and apoptosis", Annuals New York Academy of Sciences, vol. 945, pp. 239-249, (2001).

Lin, D.L, et al, "p53 is a mediator for radiation-repressed human TR2 orphan receptor expression in MCF-7 cells, a new pathway from tumor suppressor to member of the steroid receptor superfamily", J Biol Chem, vol. 271, pp. 14649-14652, (1996).

Lin, S, et al, "The biochemical status of the DNA synthesome can distinguish between permanent and temporary cell growth arrest", Cell Growth Differ, vol. 8, No. 12, pp. 1359-1369, (1997).

Little, C.D, et al, "Amplification and expression of the *c-myc* oncogene in human lung cancer lines", Nature, vol. 306, pp. 194-196, (1983).

Liu, H, et al, "Construction of a GAL1-regulated yeast cDNA expression library and its application to the identification of genes whose overexpression causes lethality in yeast", Genetics, vol. 132, No. 3, pp. 665-673, (1992).

Lovborg, H, et al, "Modulation of pyridyl cyanoguanidine (CHS 828) induced cytotoxicity by 3-aminobenzamide in U-937 GTB cells", Biochem Pharmacol, vol. 63, No. 8, pp. 1491-1498, (2002).

Mann, M, et al, "Analysis of proteins and proteomes by mass spectrometry", Annu Rev Biochem, vol. 70, pp. 437-473, (2001).

Martelli, A.M, et al, "Biochemical and Morphological characterization of the nuclear matrix from apoptotic HL-60 Cells", Journal of Cellular Biochemistry, vol. 72, No. 1, pp. 35-46, (1999).

Martelli, A.M, et al, "Behavior of nucleolar proteins during the course of apoptosis in camptothecin-treated HL60 cells", Journal of Cellular Biochemistry, vol. 78, No. 2, pp. 264-277, (2000).

Martelli, A.M, et al, "Nuclear apoptotic changes: an overview", J Cell Biochem, vol. 82, No. 4, pp. 634-646, (2001).

Martin, S.J, et al, "Protease activation during apoptosis: death by a thousand cuts?" Cell, vol. 82, pp. 349-352, (1995).

Matthews, D.A, "Adenovirus protein V induces redistribution of nucleolin and B23 from nucleolus to cytoplasm", J Virol, vol. 75, No. 2, pp. 1031-1038, (2001).

Mayer, T.U, et al, "Small molecule inhibitor of mitotic spindle bipolarity identified in a phenotype-based screen", Science, vol. 286, No. 5441, pp. 971-974, (1999).

McEwen, C.N, et al, "Negative gold ion gun for liquid secondary ion mass spectrometry", Anal Chem, vol. 57, No. 4, pp. 890-892, (1985).

McManus, M.T, et al, "Gene silencing using micro-RNA designed hairpins", RNA, vol. 8, No. 6, pp. 842-850, (2002).

McNicol, A.M, et al, "Optimizing immunohistochemistry: antigen retrieval and signal amplification", Histopathology, vol. 32, pp. 97-103, (1998).

Mi, Y, et al, "Validation of Nucleolin as a Novel Target for Cancer Drug Discovery", Proceedings of the American Association for Cancer Research Annual Meeting, vol. 43, Mar. 2002, pp. 959-960, 93rd Annual Meeting of the American Association for Cancer Research, San Francisco, California, USA, Apr. 6-10, 2002.

Mickey, D.D, et al, "Heterotransplantation of a human prostatic adenocarcinoma cell line in nude mice", Cancer Research, vol. 37, pp. 4049-4058, (1977).

Mikolajczyk, S, et al, "Tumor-associated forms of prostate specific antigen improve the discrimination of prostate cancer from benign disease", Rinsho Byori, vol. 52, No. 3, pp. 223-230, (2004).

Minota, S, et al, "Autoantibodies to nucleolin in systemic lupus erythematosus and other diseases", J Immunol, vol. 146, No. 7, pp. 2249-2252, (1991).

Miranda, G.A, et al, "The murine nucleolin protein is an inducible DNA and ATP binding protein which is readily detected in nuclear extracts of lipopolysaccharide-treated splenocytes", Exp Cell Research, vol. 217, No. 2, pp. 294-308, (1995).

Murchie, A.I, et al, "Retinoblastoma susceptibility genes contain 5' sequences with a high propensity to form guanine-tetrad structures", Nucleic Acids Research, vol. 20, No. 1, pp. 49-53, (1992).

Naito, M, et al, "ATP/$Mg^{2+}$-dependent binding of vincristine to the plasma membrane of multifrug-resistant K562 cells", J Biol Chem, vol. 263, pp. 11887-11891, (1988).

Nakanishi, K, et al, "Argyrophilic nucleolar-organizer region counts and DNA status in bronchioloalveolar epithelial hyperplasia and adenocarcinoma of the lung", Hum Pathol, vol. 29, No. 3, pp. 235-239, (1998).

Navenot, J.M, et al, "Molecular anatomy of CCR5 engagement by physiologic and viral chemokines and HIV-1 envelope glycoproteins: differences in primary structural requirements for RANTES, MIP-1 alpha, and vMIP-II Binding", J Mol Biol, vol. 313, No. 5, pp. 1181-1193, (2001).

Nichols, R.C, et al, "The RGG domain in hnRNP A2 affects subcellular localization", Exp Cell Research, vol. 256, No. 2, pp. 522-532, (2000).

Nonomura, A, et al, "Demonstration of nucleolar organizer regions in lung carcinoma by silver staining", Surgery Today, vol. 23, pp. 486-490, (1993).

Norgaard, J.M, et al, "FAB M4 and high CD14 surface expression is associated with high cellular resistance to Ara-C and daunorubicin: implications for clinical outcome in acute myeloid leukaemia", European Journal of Haematology, vol. 67, pp. 221-229, (2001).

Ohkoudo, M, et al, "Morphometrical analysis of nucleolin immunohistochemistry in meningiomas", Acta Neuropathol, vol. 92, pp. 1-7, (1996).

Orfao, A, et al, "General concepts about cell sorting techniques", Clin Biochem, vol. 29, pp. 5-9, (1996).

Paddison, P.J, et al, "Short hairpin RNAs (shRNAs) induce sequence-specific silencing in mammalian cells", Genes Dev, vol. 16, No. 8, pp. 948-958, (2002).

Palomba, L, et al, "Apoptosis and necrosis following exposure of U937 cells to increasing concentrations of hydrogen peroxide: the effect of the poly(ADP-ribose) polymerase inhibitor 3-aminobenzamide", Biochem Pharmacol, vol. 58, No. 11, pp. 1743-1750, (1999).

Pasternack, M.S, et al, "Granzyme A binding to target cell proteins Granzyme A binds to and cleaves nucleolin in vitro", J Biol Chem, vol. 266, No. 22, pp. 14703-14708, (1991).

Pich, A, et al, "Prognostic relevance of AgNORs in tumor pathology", Micron, vol. 31, No. 2, pp. 133-141, (2000).

Pinton, P, et al, "The $Ca^{2+}$ concentration of the endoplasmic reticulum is a key determinant of ceramide-induced apoptosis: significance for the molecular mechanism of Bcl-2 action", EMBO J, vol. 20, pp. 2690-2701, (2001).

Pleschke, J.M, et al, "Poly(ADP-ribose) binds to specific domains in DNA damage checkpoint proteins", J Biol Chem, vol. 275, No. 52, pp. 40974-40980, (2000).

Product Data Sheet for ab7898 from http://www.abcam.com/?datasheet=7898, (1998-2006).

Product Data Sheet for C23 (C-18): sc-9892, Santa Cruz Biotechnology, Inc, (2003).

Product Data Sheet for C23 (MS-3): sc-8031, Santa Cruz Biotechnology, Inc, (2004).

Product Data Sheet for C23 (F-18): sc-9893, Santa Cruz Biotechnology, Inc, (2003).

Product Data Sheet for Monoclonal Antibody, Anti-Nucleolin M019-3, Medical & Biological Laboratories Co, LTD, www.mblintl.com, (2003).

Product Data Sheet for Anti-Nucleolin, Clone 3G4B2, Upstate Biotechnology, http://www.upstate.com/browse/productdetail.asp?ProductId=05-565, (2005).

Puttaraju, M, et al, "Messenger RNA repair and restoration of protein function by spliceosome-mediated RNA trans-splicing", Mol Ther, vol. 4, No. 2, pp. 105-114, (2001).

Raab de Verdugo, U, et al, "Characterization of a 100-kilodalton binding protein for the six serotypes of coxsackie B viruses", Journal of Virology, vol. 69, No. 11, pp. 6751-6757, (1995).

Robinson, J.M, et al, "Antigen retrieval in cells and tissues: enhancement with sodium dodecyl sulfate", Histochem Cell Biol, vol. 116, pp. 119-130, (2001).

Rosenthal, D.S, et al, "Detection of DNA breaks in apoptotic cells utilizing the DNA binding domain of poly(ADP-ribose) Polymerase with fluorescence microscopy", Nucleic Acids Research, vol. 25, No. 7, pp. 1437-1441, (1997).

Rothenburg, S, et al, "A polymorphic dinucleotide repeat in the rat nucleolin gene forms Z-DNA and inhibits promoter activity", PNAS, vol. 98, No. 16, pp. 8985-8990, (2001).

Roussel, P, et al, "Identification of Ag-NOR proteins, markers of proliferation related to ribosomal gene activity", Experimental Cell Research, vol. 214, No. 2, pp. 465-472, (1994).

Roussel, P, et al, "Quantification of Ag-NOR proteins using Ag-NOR staining on western blots", Histochem Cytochem, vol. 42, No. 11, pp. 1513-1517, (1994).

Saijo, Y, et al, "Contiguous four-guanosine sequence in c-myc antisense phosphorothioate oligonucleotides inhibits cell growth on human lung cancer cells: possible involvement of cell adhesion inhibition", Jpn J Cancer Research, vol. 88, No. 1, pp. 26-33, (1997).

Sandoval, A, et al, "Distal recognition site for classical pathway convertase located in the C345C/netrin module of complement component C5", J Immunol, vol. 165, No. 2, pp. 1066-1073, (2000).

Schade, R, et al, "Egg yolk antibodies, State of the art and future prospects", Altex 13, supplement 96, pp. 5-9, (1996).

Schade, R, et al, "The production of avian (egg yolk) antibodies IgY. The report and recommendations of ECVAM workshop", Alternatives to laboratory animals (ALTA), vol. 24, pp. 925-934, (1996).

Schimmer, A.D, et al, "Receptor- and mitochondrial-mediated apoptosis in acute leukemia: a translational view", Blood, vol. 98, No. 13, pp. 3541-3553, (2001).

Schmidt-Acevedo, S, et al, "'LE cells' result from phagocytosis of apoptotic bodies induced by antinuclear antibodies", Journal of Autoimmunity, vol. 15, pp. 15-20, (2000).

Scovassi, A.I, et al, "Poly(ADP-ribosylation) and apoptosis", Molecular and Cellular Biochemistry, vol. 199, pp. 125-137, (1999).

Semenkovich, C.F, et al, "A protein partially expressed on the surface of HepG2 cells that binds lipoproteins specifically is nucleolin", Biochemistry, vol. 29, No. 41, pp. 9708-9713, (1990).

Shall, S, et al, "Poly(ASP-ribose) polymerase-1: what have we learned from the deficient mouse model?", Mutat Research, vol. 460, No. 1, oo, 1-15, (2000).

Shall, S, "Poly (ADP-ribosylation)-a common control process?", Bioessays, vol. 24, No. 2, pp. 197-201, (2002).

Sharma, S, et al, "Developmental of inhalational agents for oncologic use", J Clin Oncol, vol. 19, No. 6, pp. 1839-1847, (2001).

Sharp, P.A, et al, "Molecular biology. RNA interference", Science, vol. 287, No. 5462, pp. 2431-2433, (2000).

Shaw, J.P, et al, "Modified deoxyoligonucleotides stable to exonuclease degradation in serum", Nucleic Acids Res, vol. 19, No. 4, pp. 747-750, (1991).

Shi, S.R, et al, "Antigen retrieval immunohistochemistry: past, present, and future", J Histochem Cytochem, vol. 45, pp. 327-343, (1997).

Shi, S.R, et al, "Antigen retrieval techniques: current perspectives", J Histochem Cytochem, vol. 49, pp. 931-937, (2001).

Shiokawa, D, et al, "Inhibitors of poly(ADP-ribose) polymerase suppress nuclear fragmentation and apoptotic-body formation during apoptosis in HL-60 cells", FEBS Letters, vol. 413, No. 1, pp. 99-103, (1997).

Skulstad, S, et al, "Labeling of surface proteins of herpes simplex virus type 1 using a modified biotin-streptavidin system", Virus Research, vol. 37, No. 3, pp. 253-270, (1995).

Sohn, J.H, et al, "Caspase-3/CPP32 immunoreactivity and its correlation with frequency of apoptotic bodies in human prostatic carcinomas and benign nodular hyperplasias", Histopathology, vol. 37, No. 6, pp. 555-560, (2000).

Soldani, C, et al, "Poly(ADP-ribose) polymerase cleavage during apoptosis: when and where?", Exp Cell Research, vol. 269, No. 2, pp. 193-201, (2001).

Sorokina, E.A, et al, "Cloning and preliminary characterization of a calcium-binding protein closely related to nucleolin on the apical surface of inner medullary collecting duct cells", J Biol Chem, vol. 274, No. 39, pp. 27491-27496, (1999).

Srivastava, M, et al, "Molecular dissection of nucleolin's role in growth and cell proliferation: new insights", FASEB J, vol. 13, No. 14, pp. 1911-1922, (1999).

Stegh, A.H, et al, "DEDD, a novel death effector domain-containing protein, targeted to the nucleolus", EMBO J, vol. 17, No. 20, pp. 5974-5986, (1998).

Stein, C.A, "Is irrelevant cleavage the price of antisense efficacy?", Pharmacol Ther, vol. 85, No. 3, pp. 231-236, (2000).

Stein, C.A. "Keeping the biotechnology of antisense in context", Nat. Biotechnol, vol. 17, No. 3, pp. 209, (1999).

Stone, K.R, et al, "Isolation of a human prostate carcinoma cell line (DU 145)", Int J Cancer, vol. 21, pp. 274-281, (1978).

Stroun, M, et al, "About the possible orgin and mechanism of circulating DNA apoptosis and active DNA release", Clin Chim Acta, vol. 313, No. 1-2, pp. 139-142, (2001).

Stryer, L, "Levels of structure in protein architecture", Biochemistry, Third Edition, chapter 2, pp. 31-33, W.H. Freeman Company, New York, (1988).

Sundquist, W.I, et al, "Evidence for interstrand quadruplex formation in the dimerization of human immunodeficiency virus 1 genomic RNA", Proc Natl Acad Science USA, vol. 90, No. 8, pp. 3393-3397, (1993).

Sutton, V.R, et al, "Initiation of apoptosis by granzyme B requires direct cleavage of bid, but not direct granzyme B-mediated caspase activation", J Exp Med, vol. 192, No. 10, pp. 1403-1413, (2000).

Takahashi, T, et al, "p53: a frequent target for genetic abnormalities in lung cancer", Science, vol. 246, pp. 491-494, (1989).

Tentori, L, et al, "Potential clinical applications of poly(ADP-ribose) polymerase (PARP) inhibitors", Pharmacol Res, vol. 45, No. 2, pp. 73-85, (2002).

Thornberry, N.A, et al, "Caspases: enemies within", Science, vol. 281, pp. 1312-1316, (1998).

Tockman, M.S, et al, "Prospective detection of preclinical lung cancer: results from two studies of heterogeneous nuclear ribonucleoprotein A2/B1 overexpression", Clin Cancer Research, vol. 3, No. 12, pt.1, pp. 2237-2246, (1997).

Tormanen, U, et al, "Enhanced apoptosis predicts shortened survival in non-small cell lung carcinoma", Cancer Research, vol. 55, No. 23, pp. 5595-5602, (1995).

Trere, D, "AgNOR staining and quantification", Micron, vol. 31, No. 2, pp. 127-131, (2000).

Tu, G.C, et al, "Tetranucleotide GGGA motif in primary RNA transcripts. Novel target site for antisense design", J Biol Chem, vol. 273, No. 39, pp. 25125-25131, (1998).

Tuteja, N, et al, "Human DNA helicase IV is nucleolin, an RNA helicase modulated by phosphorylation", Gene, vol. 160, No. 2, pp. 143-148, (1995).

Tuteja, R, et al, "Nucleolin: a multifunctional major nucleolar phosphoprotein", Crit Rrev Biochem Mol Biol, vol. 33, pp. 407-436, (1998).

van de Loosdrecht, A.A, et al, "A tetrazolium-based colorimetric MTT assay to quantitate human monocyte mediated cytotoxicity against leukemic cells from cell lines and patients with acute myeloid leukemia", J Immunol Methods, vol. 174, pp. 311-320, (1994).

Waggoner, S, et al, "Viral ribonucleoprotein complex formation and nucleolar-cytoplasmic relocalization of nucleolin in poliovirus-infected cells", J Virol, vol. 72, No. 8, pp. 6699-6709, (1998).

Wang, Y, et al, "Regulation of dna replication after heat shock by replication protein a-nucleolin interactions", J Biol Chem, vol. 276, No. 23, pp. 20579-20588, (2001).

Wang, Z.Q, et al, "PARP is important for genomic stability but dispensable in apoptosis", Genes Dev, vol. 11, No. 18, pp. 2347-2358, (1997).

Weisenberger, D, et al, "A possible mechanism for the inhibition of ribosomal RNA gene transcription furing mitosis", J Cell Biology, vol. 129, No. 3, pp. 561-575, (1995).

White, J.R, et al, "Phosphorothioate-capped antisense oligonucleotides to Ras GAP injibit cell proliferation and trigger apoptosis but fail to downregulate GAP gene expression", Biochem Biophys Res Commun, vol. 227, No. 1, pp. 118-124, (1996).

Whittles, C.E, et al, "Apoptotic and proliferative activity in the neoplastic progression of Barrett's oesophagus: a comparative study", The Journal of Pathology, vol. 187, issue 5, pp. 535-540, (1999).

Wurzer, G, et al, "Increased resistance to anticancer therapy of mouse cells lacking the poly(ADP-ribose) polymerase attributable to up-regulation of the multidrug resistance gene product P-glycoprotein", Cancer Research, vol. 60, No. 15, pp. 4238-4244, (2000).

Wyatt, J.R, et al, "Combinatorially selected guanosine-quartet structure is a potent inhibitor of human immunodeficiency virus envelope-mediated cell fusion", Proc Natl Acad Science USA, vol. 91, No. 4, pp. 1356-1360, (1994).

Wyllie, A.H, et al, "Cell death: the significance of apoptosis", International Review of Cytology, vol. 68, pp. 251-306, (1980).

Wysocki, L.J, et al, ""Panning" for lymphocytes: a method for cell selection", Proc Natl Acad Sci USA, vol. 75, No. 6, pp. 2844-2848, (1978).

Xu, X, et al, "Inhibition of DNA replication and induction of S phase cell cycle arrest by G-rich oligonucleotides", The Journal of Biological Chemistry, vol. 276, No. 46, pp. 43221-43230, (2001).

Yao, G.Q, et al, "Identification of two oligodeoxyribonucleotide binding proteins on plasma membranes of human cell lines", Biochemical Pharmacology, vol. 51, pp. 431-436, (1996).

Xiao-Ming, Y., "Signal transduction mediated by Bid, a pro-death Bcl-2 family proteins, connects the death receptor and mitochondria apoptosis pathways", Cell Research, vol. 10, No. 3, pp. 161-167, (2000).

European Search Report dated Oct. 25, 2006 for PCT application No. PCT/US03/20167.

Mi, Y., et al., "Apoptosis in Leukemia cells is accompanied by alterations in the levels and localization of Nucleolin", The Journal of Biological Chemistry, vol. 278, No. 10, pp. 8572-8579, (2003).

Rosen, A., et al., "Autoantigens as substrates for apoptotic proteases: implications for the pathogenesis of systemic autoimmune disease", Cell Death and Differentiation, vol. 6, No. 1, pp. 6-12, (1999).

Masters, J.R.W., "Human cancer cell lines: fact and fantasy", Nature Reviews Molecular Cell Biology, vol. 1, pp. 233-236, (2000).

Agrawal, S, et al, "Antisense therapeutics: is it as simple as complementary base recognition?", Mol Med Today, vol. 6, No. 2, pp. 72-81, (2000).

Aihara, M, et al, "Frequency of apoptotic bodies positively correlateswith Gleason grade in prostate cancer", Hum Pathol, vol. 25, No. 8, pp. 797-801, (1994).

Altman, S, "Nobel lecture. Enzymatic cleavage of RNA by RNA", Biosci Rep, vol. 10, No. 4, pp. 317-337, (1990).
Andrade, F, et al, "Apoptosis in systemtic lupus erythematosus", Rheumatic Diseases Clinics of North America, vol. 2, (2000).
Awang, G, et al, "Mode of dimerization of HIV-1 genomic RNA", Biochemistry, vol. 32, No. 42, pp. 11453-11457, (1993).
Barton, C.M, et al, "Antisense oligonucleotides directed against p53 have antiproliferative effects unrelated to effects on p53 expression", Br J Cancer, vol. 71, No. 3, pp. 429-437, (1995).
Beedassy, A, et al, "Chemotherapy in advanced prostate cancer", Semin Oncol, vol. 26, No. 4, pp. 428-438, (1999).
Bergsmedh, A, et al, "Horizontal transfer of oncogenes by uptake of apoptotic bodies", Proc Natl Acad Science USA, vol. 98, No. 11, pp. 6407-6411, (2001).
Bernardi, F.D, et al, "A prognostic model of survival in surgically resected squamous cell carcinoma of the lung using clinical, pathologic, and biologic markers", Mod Pathol, vol. 10, No. 10, pp. 992-1000, (1997).
Blau, H.M, et al, "Tet B or not tet B: Advances in tetracycline-inducible gene expression", Proc Natl Acad Science USA, vol. 96, pp. 797-799, (1999).
Borer, R.A, et al, "Major nucleolar proteins shuttle between nucleus and cytoplasm", Cell, vol. 56, No. 3, pp. 379-390, (1989).
Borst, P, et al, "Does resistance to apoptosis affect clinical response to antitumor drugs?", Drug Resist Update, vol. 4, No. 2, pp. 129-131, (2001).
Brown, J.M, et al, "Apoptosis:mediator or mode of cell killing by anticancer agents?", Drug Resist Update, vol. 4, No. 2, pp. 135-136, (2001).
Brustmann, H, "Apoptotic bodies as a morphological feature in serous ovarian carcinoma: correlation with nuclear grade, Ki-67 and mitotic indices", Pathol Res Pract, vol. 198, No. 2, pp. 85-90, (2002).
Burgess, T.L, et al, "The antiproliferative activity of c-myb and c-myc antisense oligonucleotides in smooth muscle cells is caused by a nonantisense mechanism", Proc Natl Acad Science USA, vol. 92, No. 9, pp. 4051-4055, (1995).
Cech, T.R, "Biologic catalysis by RNA", Harvey Lect, vol. 82, pp. 123-144, (1988).
Chern, J.H, et al, "Usefulness of AgNOR score in differentiating benign from malignant pulmonary aspiration cytology", Acta Cytol, vol. 41, No. 2, pp. 393-398, (1997).
Cole, S.P, et al, "Antibody production by human X human hybridomas in serum-free medium", J Immunol Methods, vol. 78, No. 2, pp. 271-278, (1985).
Crooke, S, "Progress in antisense technology: the end of the beginning", Methods Enzymol, vol. 313, pp. 3-45, (1999).
Dagle, J.M, et al, "Selective degradation of targeted mRNAs using partially modified oligonucleotides", Methods Enzymol, vol. 313, pp. 420-436, (1999).
Daniely, Y, et al, "Formation of a complex between nucleolin and replication protein A after cell stress prevents initiation of DNA replication", J Cell Biology, vol. 149, No. 4, pp. 799-810, (2000).
Deng, J.S, et al, "Internalization of anti-nucleolin antibody into viable HEp-2 cells", Mol Biol Rep, vol. 23, No. 3-4, pp. 191-195, (1996).
Derezini, M, et al, "The quantity of nucleolar proteins nucleolin and protein B23 is related to cell doubling time in human cancer cells", Lab Invest, vol. 73, No. 4, pp. 497-502, (1995).
Eguchi, K, "Apoptosis in autoimmune diseases", Intern Med, vol. 40, No. 4, pp. 275-284, (2001).
Fielding, P, et al, "Heterogeneous nuclear ribonucleoprotein A2/B1 up-regulation in bronchial lavage specimens: a clinical marker of early lung cancer detection", Clinical Cancer Research, vol. 5, No. 12, pp. 4048-4052, (1999).
Fry, M, et al, "The fragile X syndrome d(CGG)n nucleotide repeats form a stable tetrahelical structure", Proc Natl Acad Science USA, vol. 91, No. 11, pp. 4950-4954, (1994).
Gautier, F, et al, "Identification of an apoptotic cleavage product of BARD1 as an autoantigen: a potential factor in the antitumoral response mediated by apoptotic bodies", Cancer Research, vol. 60, No. 24, pp. 6895-6900, (2000).
Hanahan, D, et al, "The hallmarks of cancer", Cell, vol. 100, No. 1, pp. 57-70, (2000).

Hanakahi, L.A, et al, "Nucleolin is one component of the B cell-specific transcription factor and switch region binding protein, LR1", Proc Natl Acad Science USA, vol. 94, No. 8, pp. 3605-3610, (1997).
Hirsch, F.R, et al, "Early detection of lung cancer: clinical perspectives of recent advances in biology and radiology", Clinical Cancer Research, vol. 7, No. 1, pp. 5-22, (2001).
Iida, A, et al, "Inducible gene expression by retrovirus-mediated transfer of a modified tetracycline-regulated system", J Birol, vol. 70, No. 9, pp. 6054-6059, (1996).
Ishikawa, F, et al, "Nuclear proteins that bind the pre-mRNA 3' splice site sequence r(UUAG/G) and the human telomeric DNA sequence d(TTAGGG)n", Mol Cell Biology, vol. 13, No. 7, pp. 4301-4310, (1993).
Kamma, H, et al, "Interaction of hnRNP A2/B1 isoforms with telomeric ssDNA and the in vitro function", Biochem Biophys Res Commun, vol. 280, No. 3, pp. 625-630, (2001).
Kaneko, S, et al, "Nucleolar organizer regions as a prognostic indicator for stage I non-small cell lung cancer", Cancer Research, vol. 51, No. 15, pp. 4008-4011, (1991).
Keough, T, et al, "A method for high-sensitivity peptide sequencing using postsource decay matrix-assisted laser desorption ionization mass spectrometry", Proc Natl Acad Science USA, vol. 96, No. 13, pp. 7131-7136, (1999).
Ketting, R.F, et al, "Dicer functions in RNA interference and in synthesis of small RNA involved in developmental timing in C elegans", Genes Dev, vol. 15, No. 20, pp. 2654-2659, (2001).
Kibbey, M.C, et al, "A 110-kD nuclear shuttling protein, nucleolin, binds to the neurite-promoting IKVAV site of laminin-1", J Neurosci Research, vol. 42, No. 3, pp. 314-322, (1995).
Kohler, G, et al, "Continuous cultures of fused cells secreting antibody of predefined specificity", Nature, vol. 256, pp. 495-497, (1975).
Kohler, P.O, "Isolation, cloning, and hybridization of endocrine cell lines", Methods Enzymol, vol. 39, pp. 109-128, (1975).
Krantz, S, et al, "Purification and partial amino acid sequencing of a fructosyllysine-specific binding protein from cell membranes of the monocyte-like cell line U937", Biochim Biophys Acta, vol. 1266, No. 1, pp. 109-112, (1995).
Kumar, R.K, et al, "Improved double immunofluorescence for confocal laser scanning microscopy", J Histochem Cytochem, vol. 47, No. 9, pp. 1213-1218, (1999).
Lakka, S.S, et al, "Adenovirus-mediated antisense urokinase-type plasminogen activator receptor gene transfer reduces tumor cell invasion and metastasis in non-small cell lung cancer cell lines", Clinical Cancer Research, vol. 7, No. 4, pp. 1087-1093, (2001).
Larrucea, S, et. al, "Internalization of factor J and and cellular signalization after factor J-cell interaction", Biochem Biophys Res Commun, vol. 266, No. 1, pp. 51-57, (1999).
Lebedeva, I, et al, "Antisense oligonucleotides: promise and reality", Annu Rev Pharmacol Toxicol, vol. 41, pp. 403-419, (2001).
Lopes de Menezes, D, et al, "Pharmacokinetics of Bcl-2 antisense oligonucleotide (G3139) combined with doxorubicin in SCID mice bearing human breast cancer solid tumor xenografts", Cancer Chemother Pharmacol, vol. 49, No. 1, pp. 57-68, (2002).
Ma J, et al, "Cells designed to deliver anticancer drugs by apoptosis", Cancer Research, vol. 62, No. 5, pp. 1382-1387, (2002).
McManus, M.T, et al, "Gene silencing in mammals by small interfering RNAs." Nat Rev Genet, vol. 3, No. 10, pp. 737-747, (2002).
Mehes, G, et al, "Nucleolin and fibrillarin expression in stimulated lymphocytes and differentiating HL-60 cells. A flow cytometric assay", Cell Prolif, vol. 28, No. 6, pp. 329-336, (1995).
Morgan, D.M, "Tetrazolium (MTT) assay for cellular viability and activity", Meth Mol Biol, vol. 79, pp. 179-183, (1998).
Morimoto, Y, et al, "Alteration of argyrophilic nucleolar organizer region associated (Ag-NOR) proteins in apoptosis-induced human salivary gland cells and human oral aquamous carcinoma cells", J Oral Pathol Med, vol. 30, No. 4, pp. 193-199, (2001).
Morimoto, Y, et al, "Upregulation of the expression of Fas antigen and Fas ligand in a juman submandibular gland ductal cell line by okadaic acid", Arch Oral Biol, vol. 45, No. 8, pp. 657-666, (2000).
Neuberger, M.S, et al, "Recombinant antibodies possessing novel effector functions", Nature, vol. 312, No. 5995, pp. 604-608, (1984).

Nosseri, C, et al, "Possible involvement of poly(ADP-ribosyl) polymerase in triggering-stress-induced apoptosis", Exp Cell Research, vol. 212, No. 2, pp. 367-373, (1994).

Oyama, T, et al, "Nucleolar organizer regions are independently associated with a shortened survival in patients with non-small cell lung cancer", Surg Oncol, vol. 2, No. 6, pp. 341-347, (1993).

Paddison, P.J, et al, "Stable suppression of gene expression by RNAi in mammalian cells", Proc Natl Acad Science USA, vol. 99, No. 3, pp. 1443-1448, (2002).

Pandey, A, et al, "Proteomics to study genes and genomes", Nature, vol. 405, No. 6788, pp. 837-846, (2000).

Perry, S.W, et al, "Simultaneous in situ detection of apoptosis and necrosis in monolayer cultures by TUNEL and trypan blue staining", Biotechniques, vol. 22, No. 6, pp. 1102-1106, (1997).

Platt, N, et al, "Recognizing death: the phagocytosis of apoptotic cells", Trends Cell Biology, vol. 8, No. 9, pp. 365-372, (1998).

Richardson, D.S, et al, "Effects of PARP inhibition on drug and Fas-induced apoptosis in leukaemic cells", Adv Exp Med Biol, vol. 457, pp. 267-279, (1999).

Roninson, I.B, et al, "If not apoptosis, then what? Treatment-induced senescence and mitotic catastrophe in tumor cells", Drug Resist Update, vol. 4, No. 5, pp. 303-313, (2001).

Saikumar, P, et al, "Apoptosis: definition, mechanisms, and relevance to disease", Am J Med, vol. 107, No. 5, pp. 489-506, (1999).

Schmitt, C.A, et al, "Apoptosis is critical for drug response in vivo", Drug Resist Update, vol. 4, No. 2, pp. 132-134, (2001).

Sciavolino, P.J, et al, "Molecular biology of prostate development and prostate cancer", Ann Med, vol. 30, No. 4, pp. 357-368, (1998).

Sen, D, et al, "Formation of parallel four-stranded complexes by guanine-rich motifs in DNA and its implications for meiosis", Nature, vol. 334, No. 6180, pp. 364-366, (1988).

Sharp, P.A, "RNA interference—2001" Genes Dev, vol. 15, No. 5, pp. 485-490, (2001).

Simbulan-Rosenthal, C.M, et al, "Involvement of PARP and poly(ADP-ribosyl)ation in the early stages of apoptosis and DNA replication", Mol Cell Biochem, vol. 193, No. 1-2, pp. 137-148, (1999).

Sirri, V, et al, "Amount variability of total and individual Ag-NOR proteins in cells stimulated to proliferate", Histochem Cytochem, vol. 43, No. 9, pp. 887-893, (1995).

Smulson, M.E, et al, "Roles of poly(ADP-ribosyl)ation and PARP in apoptosis, DNA repair, genomic stability and functions of p52 and E2F-1", Adv Enzyme Regul, vol. 40, pp. 183-215, (2000).

Sperandio, S, et al, "An alternative, nonapoptotic form of programmed cell death", Proc Natl Acad Science USA, vol. 97, No. 26, pp. 14376-14381, (2000).

Srinivasan, S.K, et al, "Review of in vivo pharmacokinetics and toxicology of phosphorothioate oligonucleotides", J Clin Lab Anal, vol. 9, No. 2, pp. 129-137, (1995).

Stein, C.A, et al, "Phosphorothioate oligodeoxynucleotides-antisense inhibitors of gene expression?", Pharmacol Ther, vol. 52, No. 3, pp. 365-384, (1991).

Summerton, J, et al, "Morpholino antisense oligomers: design, preparation, and properties", Antisense Nucleic Acid Drug Development, vol. 7, No. 3, pp. 187-195, (1997).

Sundquist, W.I, et al, "Telomeric DNA dimerizes by formation of guanine tetrads between hairpin loops", Nature, vol. 342, No. 6251, pp. 825-829, (1989).

Symons, R.H. "Small catalytic RNAS", Annual Review Biochem, vol. 61, pp. 641-671, (1992).

Tanaka, Y, et al, "Inhibition and down-regulation of poly(ADP-ribose) polymerase results in a marked resistance of HL-60 cells to various apoptosis-inducers", Cell Mol Biol, vol. 41, No. 6, pp. 771-781, (1995).

Templin, M.V, et al, "Pharmacokinetic and toxicity profile of a phosphorothioate oligonucleotide following inhalation delivery to lung in mice", Antisense Nucleic Acid Drug Dev, vol. 10, No. 5, pp, 359-368, (2000).

Tockman, M.S, et al, "Sensitive and specific monoclonal antibody recognition of human lung cancer antigen on preserved sputum cells: a new approach to early lung cancer detection", J Clin Oncol, vol. 6, No. 11, pp. 1685-1693, (1988).

Wang, W, et al, "A comparison of guanosine-quartet inhibitory effects versus cytidine homopolymer inhibitory effects on rat neointimal formation", Antisense Nucleic Acid Drug Development, vol. 8, No. 3, pp. 227-236, (1998).

Wang, Y, et al, "Solution structure of the human telomeric repeat d[AG3(T2AG3)3] G-tetraplex", Structure, vol. 1, No. 4, pp. 263-282, (1993).

Williamson, J.R, et al, "Monovalent cation-induced structure os telomeric DNA: the G-quartet model", Cell, vol. 59, No. 5, pp. 871-880, (1989).

Winter, G, et al, "Making antibodies by phage display technology", Annu Rev Immunol, vol. 12, pp. 433-455, (1994).

Wolters, D.A, et al, "An automated multidimensional protein identification technology for shotfun proteomics", Anal Chem, vol. 73, No. 23, pp. 5683-5690, (2001).

Xue, Z, et al, "The amino terminus of mammalian nucleolin specifically recognizes SV40 T-antigen type nuclear localization sequences", Eur J Cell Biol, vol. 62, No. 1, pp. 13-21, (1993).

Yanagida, M, et al, "Isolation and proteomic characterization of the major proteins of the nucleolin-binding ribonucleoprotein complexes", Proteomics, vol. 1, No. 11, pp. 1390-1404, (2001).

Coligan, J.E. et al, "Production of Monoclonal Antibodies", Current Protocols in Immunology, vol. 1, pp. 2.5.1-2.6.7, Wiley, New York, (1991).

Crooke, S, "Oligonucleotide therapeutics: a prospectus" Antisense Research and Development, vol. 3, No. 1, pp. 1-2, (1993).

Gilloteaux, J. et al., "Cancer cell necrosis by autoschizis: Synergism of antitumor activity of vitamin C: vitamin K3 on human bladder carcinoma T24 cells", Scanning, vol. 20, No. 8, pp. 564-575, (1998).

Giovannangeli, C. et al., "Progress in developments of triplex-based strategies", Antisense & Nucleic Acid Drug Development, vol. 7, No. 4, pp. 413-421, (1997).

Knorre, D.G, et al, "Antisense oligonucleotide derivatives as gene-targeted drugs", Biomed Sci, vol. 1, No. 4, pp. 334-343, (1990).

Mattson, M.P., "Apoptosis in neurodegenerative disorders", Nature Reviews Mol Cell Biology, vol. 1, No. 2, pp. 120-129, (2000).

Morrison, S.L. et al., "Chimeric human antibody molecules: mouse antigen-binding domains with human constant region domains", Proceedings of the National Academy of Science USA, vol. 81, No. 21, pp. 6851-6855, (1984).

Partridge, M. et al., "A simple method for delivering morpholino antisense oligos into the cytoplasm of cells", Antisense & Nucleic Acid Drug Development, vol. 6, No. 3, pp. 169-175, (1996).

Sherwood, J.K. et al, "Controlled antibody delivery systems", Biotechnology, vol. 10, No. 11, pp. 1446-1449, (1992).

Soldani, C. et al., "Two-color fluorescence detection of Poly (ADP-ribose) polymerase-1 (PARP-1) cleavage and DNA strand breaks in etoposide-induced apoptotic cells", Eur J Histochem, vol. 45, No. 4, pp. 389-392, (2001).

International Search Report and Written Opinion of the International Searching Authority for PCT/US2004/033174 dated Mar. 14, 2005.

Mi, Yingchang, et al., "Validation of Nucleolin as a Novel Target for Cancer Drug Discovery", Proceedings of the American Association for Cancer Research Annual Meeting, vol. 43, Mar. 2002, pp. 959-960—abstract & 93rd Annual Meeting of the American Association for Cancer Research, San Francisco, California, USA, Apr. 6-10, 2002.

Grinstein, Edgar, et al., "Nucleolin as Activator of Human Papillomavirus Type 18 Oncogene Transcription in Cervical Cancer", J. Exp. Med., vol. 196, No. 8, Oct. 21, 2002, The Rockefeller University Press, pp. 1067-1078.

* cited by examiner

METHOD FOR THE DIAGNOSIS AND PROGNOSIS OF MALIGNANT DISEASES

FEDERALLY SPONSORED RESEARCH OR DEVELOPMENT

This subject matter of this application may have been funded in part under the following research grants and contracts: National Institutes of Health 1 R21 CA 91115, and Department of Defense DAMD17-98-1-8583 and DAMD17-01-1-0067. The U.S. Government may have rights in this invention.

The invention is based on the discovery of a correlation between nucleolin cellular plasma membrane expression and the presence and aggressiveness of neoplastic cells. Thus, the invention is drawn to the detection and prognosis of pre-malignant conditions and malignant diseases and disorders and kits for detection and prognosis.

BACKGROUND

Being well-prepared for battle engenders success; when the foe is cancer, early detection results in a greater likelihood that medical intervention will be successful. At early stages, treatments can often be targeted only to the affected tissues, diminishing side effects. If not caught early, cancer cells may metastasize and spread throughout the body. The prognosis in this case is more dire, and medical treatments are often applied systemically, killing not only cancer cells, but large numbers of healthy cells.

A hallmark of a cancer cell is uncontrolled proliferation. Cancer cells may also exhibit morphological and functional aberrations. Cancer cells may display less organized cellular morphology; for example, losing the asymmetric organelle and structural organization (cell polarity) that allows for proper cell function. Cell-cell and cell-substratum contacts, the specificities of which are also necessary for normal function, are often modulated or lost. Functionally, the cells may carry on few, if any, wild-type functions, or may have exaggerated, unregulated normal functions, such as hormone secretion. Such cells regress to early developmental stages, appearing less differentiated than their wild-type (i.e., normal) parents.

Cancer cells also often mis-express or mis-target proteins to inappropriate cellular compartments. Proteins may be up- or down-regulated; even proteins not usually expressed by a specific cell type can be expressed by the transformed counterpart. Protein mis-expression can have a plethora of downstream cellular effects, including drastic changes in membrane composition, organelle formation, or physiology. Mis-targeting of proteins (and other molecules, such as lipids, etc.) also contributes to the loss of cell polarity.

Detecting cancer growths are complicated by a variety of factors, including protein mis-expression and cellular dedifferentiation. For example, cancers can proceed gradually, being present in only small numbers that are difficult to detect. A common diagnostic approach is the use of certain proteins as "markers" to distinguish cancer cells from healthy ones. For example, prostate cancer diagnoses often use prostate-specific antigen (PSA). These assays require that a marker be defined, have detection agents, and be readily available. However, a marker that is present in a many, if not most, cancers has yet to be defined. Such a marker would remarkably facilitate diagnosis.

SUMMARY

In a first aspect, the invention is drawn to methods of determining a neoplastic state of a cell, comprising detecting the presence of nucleolin on the plasma membrane of a cell, including mammalian cells, such as human; the cell may also be lysed. Plasma membrane nucleolin is detected by using an anti-nucleolin agent, such as anti-nucleolin antibodies or oligonucleotides, including those of sequences of SEQ ID NOs: 1-7; 9-17; 19-31.

In a second aspect, the invention is drawn to methods of determining a phenotype of a neoplastic cell, comprising quantifying the amount of plasma membrane nucleolin of the cell, including mammalian cells, such as human; the cell may also be lysed. Plasma membrane nucleolin is detected by using an anti-nucleolin agent, such as anti-nucleolin antibodies or oligonucleotides, including those of sequences of SEQ ID NOs:1-7; 9-17; 19-31.

In another aspect, the invention is drawn to kits for determining a neoplastic state of a cell, comprising an anti-nucleolin agent and a control sample. Such kits may also contain reagents that bind to nucleolin, reagent-nucleolin complexes and other components, such as a fixative, a buffer, plasticware, serum, serum albumin, non-fat milk, membranes and instructions.

In another aspect, the invention pertains to methods of detecting small lung cell carcinoma in a subject, comprising collecting a sample containing lung cells from a subject; and detecting the presence of plasma membrane nucleolin in the cells. Samples include sputum; subjects may be human.

In yet another aspect, the invention is drawn to methods of diagnosing tumor, pre-malignant or malignant cells, comprising collecting a sample from a subject comprising cells, sending the sample to a testing center, determining the neoplastic state of the cells by probing for cell plasma membrane nucleolin.

DETAILED DESCRIPTION

Figure 1:
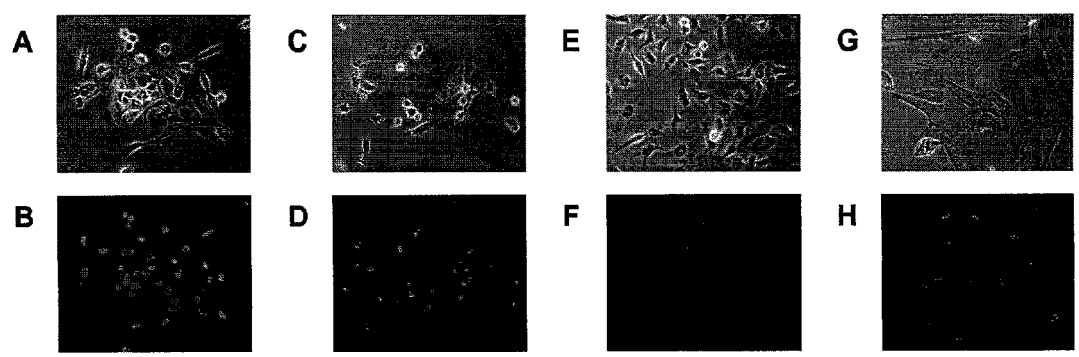
FIG. 1 shows nuclear nucleolin staining in various cell lines. Shown are immunofluorescent (B, D, F, H) and parallel phase contrast micrographs (A, C, E, G). Cell lines that were analyzed were: DU145 prostate cancer cells (A, B), MDA-MB-231 breast cancer cells (C, D), HeLa cervical cancer cells (E, F) and HS27 normal skin cells (G, H). An anti-nucleolin antibody was used; the cells were permeabilized before staining to allow the antibody access to the cytoplasmic and nuclear compartments.

The invention is based on the discovery of a correlation between nucleolin plasma membrane expression and the presence and aggressiveness of neoplastic cells.

The invention provides compositions and methods for the detection of neoplastic cells, such as malignant and pre-malignant cells, using a neoplastic antigen that is broadly expressed, nucleolin. However, the expression of nucleolin is insufficient to indicate malignancy (nucleolin is found in every nucleated cell); but the localization of nucleolin on the cell surface is indicative. While increased amounts of nuclear nucleolin, as visualized by silver staining, has been used as a diagnostic tool for cancer, the unexpected discovery that nucleolin found on the cell surface correlates with a pre-malignant or malignant phenotype can facilitate cancer diagnosis and prognosis.

The advantages of using surface-localized nucleolin include:

(1) Improved accuracy. Assaying for plasma membrane nucleolin more accurately identifies the malignant phenotype compared to silver-staining for nuclear nucleolin.

(2) Specificity. Plasma membrane nucleolin is not normally observed in the plasma membrane of most wild-type (healthy) cells. Thus, unlike many other diagnostic tests that require analyzing the amount of a marker, plasma membrane nucleolin detection can be used qualitatively. A more fail-proof "yes-no" type of test is therefore feasible. This aspect also allows for testing on both single cells and tissue samples.

(3) Broad applicability. Many different cancers may be detected by examining for plasma membrane nucleolin.

(4) Multifunctional. The methods are prognostic as well as diagnostic: the rate of cellular proliferation typically correlates with levels of plasma membrane nucleolin.

While investigating the anti-proliferative activity of non-antisense guanosine-rich oligonucleotides (GROs) on cancer cells, it was found that such anti-proliferative GROs bind nucleolin to exert their effects (Bates et al., 1999; Miller et al., WO 00/61597, 2000). Nucleolin (Bandman et al., U.S. Pat. No. 5,932,475, 1999) is an abundant, non-ribosomal protein of the nucleolus, the site of ribosomal gene transcription and packaging of pre-ribosomal RNA. This 707 amino acid phosphoprotein has a multi-domain structure consisting of a histone-like N-terminus, a central domain containing four RNA recognition motifs and a glycine/arginine-rich C-terminus and has an apparent molecular weight of 110 kD. Its multiple domain structure reflects the remarkably diverse functions of this multifaceted protein (Ginisty et al., 1999; Srivastava and Pollard, 1999; Tuteja and Tuteja, 1998). Nucleolin has been implicated in many fundamental aspects of cell survival and proliferation. Most understood is the role of nucleolin in ribosome biogenesis. Other functions may include nucleocytoplasmic transport, cytokinesis, nucleogenesis and apoptosis.

Nucleolin synthesis has been correlated with increased rates of cell division (cell proliferation); nucleolin levels are therefore higher in tumor cells compared to most normal cells (Tuteja and Tuteja, 1998). Nucleolin is one of the nuclear organizer region (NOR) proteins whose levels, as measured by silver staining, are assessed by pathologists as a marker of cell proliferation and an indicator of malignancy (Derenzini, 2000).

Also present in the cell plasma membrane in a few cell types, such as lymphocytes and inner medullary collecting duct cells, nucleolin has been hypothesized to function as a receptor (e.g., Callebaut et al., 1998; Sorokina and Kleinman, 1999). However, the role of plasma membrane nucleolin is not well understood. In addition, it is not clear whether the plasma membrane nucleolin is identical to the nucleolar protein, or if it represents a different isoform or nucleolin-like protein. However, the expression of plasma membrane nucleolin is specific to neoplastic cells (such as malignant or pre-malignant); thus the function of plasma membrane nucleolin need not be known for diagnostic and prognostic purposes.

Definitions

Neoplasm, Malignancy, Tumor, Cancer Cells

A neoplasm is an abnormal tissue growth resulting from neoplastic cells, cells that proliferate more rapidly and uncontrollably than normal cells. Usually partially or completely structurally disorganized, neoplasms lack functional coordination with the corresponding normal tissue. Neoplasms usually form a distinct tissue mass that may be either benign (tumor) or malignant (cancer).

Cancer cells invade surrounding tissues, may metastasize to distant sites, and are likely to recur after attempted removal, causing death of a subject if not adequately treated. In addition to structural disorganization, cancer cells usually regress to more primitive or undifferentiated states (anaplasia), although morphologically and biochemically, they may still exhibit many functions of the corresponding wild-type cells. Carcinomas are cancers derived from epithelia; sarcomas are derived from connective tissues.

Cancers may be more aggressive or less aggressive. The aggressive phenotype of a cancer cell refers to the proliferation rate and the ability to form tumors and metastasize in nude mice. Aggressive cancers proliferate more quickly, more easily form tumors and metastasize than less-aggressive tumors.

Neoplastic State

The term "neoplastic state" refers to three conditions: normal, pre-malignant and malignant. "Normal" refers to a growth or cell that is clinically normal (healthy). "Pre-malignant" refers to a growth or cell that is on the pathway to malignancy, but at the time of examination, would not be classified as malignant by conventional methods. "Malignant" refers to a cell or growth that has at least one of the following properties: locally invasive, destructive growth and metastasis.

GROs and Other Polypeptide-Binding Oligonucleotides

Oligonucleotides are available that specifically bind to polypeptides, such as nucleolins. Examples of such are GROs, which are guanosine-rich oligonucleotides. Characteristics of GROs include:

(1) having at least 1 GGT motif
(2) preferably having 4-100 nucleotides, although GROs having many more nucleotides are possible
(3) having chemical modifications to improve stability.

Especially useful GROs form G-quartet structures, as indicated by a reversible thermal denaturation/renaturation profile at 295 nm (Bates et al., 1999). Preferred GROs also compete with a telomere oligonucleotide for binding to a target cellular protein in an electrophoretic mobility shift assay (Bates et al., 1999).

Other oligonucleotides may have high binding specificity for nucleolin.

Anti-Nucleolin Agent

An "anti-nucleolin agent" binds to nucleolin. Examples include anti-nucleolin antibodies and certain oligonucleotides.

Embodiments

The following embodiments are given as examples of various ways to practice the invention. Many different ways of practicing the invention are also possible.

In all embodiments, the underlying principle is to specifically differentiate between plasma membrane nucleolin and nuclear nucleolin. Plasma membrane nucleolin, as discovered by the applicants, correlates with cells that are in a neoplastic state; furthermore, the amount of plasma membrane nucleolin also indicates the aggressiveness of these cells; that is, the higher the plasma membrane nucleolin expression, the more aggressive the cells. Various techniques allow a user to differentiate between nuclear and plasma membrane nucleolin. Detection techniques, wherein the nucleolin-detecting reagents have exclusive access to extracellular portions of the cell (and consequently cell-plasma membrane nucleolin), or biochemical techniques, wherein either the surface plasma membrane and/or surface proteins are separated from other cellular components and compartments, are also useful.

In an embodiment, nucleolin is detected directly on the cell surface. A cell is isolated from a subject and plasma membrane nucleolin detected using an agent that binds nucleolin. Cells may be isolated by any known technique. An isolated cell may comprise a larger tissue sample containing cells that are not neoplastic. Detection procedures use anti-nucleolin antibodies that bind extracellular nucleolin epitopes; these antibodies may be directly labeled or when bound, detected indirectly. Other useful plasma membrane nucleolin detection agents include GROs that specifically bind nucleolin. Useful procedures, such as fluorescence-activated cell sorting (FACS) or immunofluorescence, employ fluorescent labels, while other cytological techniques, such as histochemical, immunohistochemical and other microscopic (electron microscopy (EM), immuno-EM) techniques use various other labels, either colorimetric or radioactive. The various reagents may be assembled into kits.

In another embodiment, cells are isolated from a subject and extracted. Plasma membranes and/or proteins are then isolated (such as via differential extraction, or differential physical cell disruption, differential centrifugation of detergent-extracted cells, etc.), and then nucleolin detected in the isolated membranes using an agent that binds nucleolin. In general, useful techniques to detect nucleolin include those wherein the extract is placed on a substrate, and the substrate probed with a nucleolin-detecting reagent. Examples of such techniques include polypeptide dot blots and Western blots, biochips, protein arrays, etc. Other detection formats include enzyme-linked immunosorbent assays (ELISAs) in their manifold manifestations (Ausubel et al., 1987). In embodiments wherein plasma membrane surface molecules are physically separated from most of the other cellular components and compartments, the nucleolin-binding agents need not specifically recognize any extracellular portions of nucleolin. The various reagents may be assembled into kits.

In a further embodiment, the methods of the invention are directed to detecting lung cancer, such as lung small cell carcinomas. Plasma membrane nucleolin expression is useful for detection and prognosis.

In yet another embodiment, methods of treating cells in a neoplastic state including cancer and tumor cells are provided, exploiting plasma membrane nucleolin that acts as a beacon. Administration of anti-nucleolin antibodies, which may be conjugated to a toxin or other means of stimulating cell death or incurring cell necrosis, results in the removal of plasma membrane nucleolin-expressing cells.

Practicing the Invention

The methods of the invention include in part the steps of collecting cells from a subject and detecting plasma membrane nucleolin. The following, not meant to limit the invention, is presented to aid the practitioner in carrying out the invention, although other methods, techniques, cells, reagents and approaches can be used to achieve the invention.

Cells

Cells or tissue samples are collected from a subject. The subject is a vertebrate, more preferably a mammal, such as a monkey, dog, cat, rabbit, cow, pig, goat, sheep, horse, rat, mouse, guinea pig, etc.; and most preferably a human. Any technique to collect the desired cells may be employed, including biopsy, surgery, scrape (inner cheek, skin, etc.) and blood withdrawal. Any appropriate tool may be used to carry out such tasks. It is not necessary to isolate the test population (i.e., those cells being tested for neoplastic state) from those cells and tissues (contaminating material) that are not being tested, except in some cases using biochemical methods that include extraction. In this last case, the test population need not be completely isolated from contaminating materials, but should either predominate or be easily distinguishable (e.g., morphologically (structurally, specific markers) or biochemically).

For those methods that analyze lung carcinomas, sputum collection is an attractive and easily obtained sample. The term "sputum" as used herein refers to expectorated matter made up of saliva and discharges from the respiratory airways. Sputum is a highly complex material that has a pronounced gel-like structure.

For collection of sputum, Byrne, et al., (Byrne, 1986) suggest that the patient collect material, raised by several deep coughs, in a container with a lid. Alternatively, sputum can be collected by using a bronchoscope (Kim et al., 1982). Specific devices or agents may be used to facilitate sputum collection (Babkes et al., U.S. Pat. No. 6,325,785, 2001; King and Speert, U.S. Pat. No. 6,339,075, 2002; Rubin and Newhouse, U.S. Pat. No. 5,925,334, 1999). Other methods of sputum collection are also available.

Cell Culture

In some cases, culturing the harvested cells is desirable to augment their numbers so that plasma membrane nucleolin detection is facilitated. Suitable media and conditions for generating primary cultures are well known. The selection of the media and culture conditions vary depending on cell type and may be empirically determined. For example, skeletal muscle, bone, neurons, skin, liver, and embryonic stem cells are grown in media that differs in their specific contents. Furthermore, media for one cell type may differ significantly from laboratory to laboratory and institution to institution. To keep cells dividing, serum, such as fetal calf serum (FCS) (also known as fetal bovine serum (FBS)), is added to the medium in relatively large quantities, 5%-30% by volume, depending on cell or tissue type. Other sera include newborn calf serum (NCS), bovine calf serum (BCS), adult bovine serum (ABS), horse serum (HS), human, chicken, goat, porcine, rabbit and sheep sera. Serum replacements may also be used, such as controlled process serum replacement-type (CPSR; 1 or 3) or bovine embryonic fluid. Specific purified growth factors or cocktails of multiple growth factors can also be added or sometimes substituted for serum. Specific factors or hormones that promote proliferation or cell survival can also be used.

Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, and Medium 199. A medium specifically developed for a particular cell type/line or cell function, e.g. Madin-Darby Bovine Kidney Growth Medium, Madin-Darby Bovine Kidney Maintenance Medium, various hybridoma media, Endothelial Basal Medium, Fibroblast Basal Medium, Keratinocyte Basal Medium, and Melanocyte Basal Medium are also known. If desired, a protein-reduced or -free and/or serum-free medium and/or chemically defined, animal component-free medium may be used, e.g., CHO, Gene Therapy Medium or QBSF Serum-free Medium (Sigma Chemical Co.; St. Louis, Mo.), DMEM Nutrient Mixture F-12 Ham, MCDB (105, 110, 131, 151, 153, 201 and 302), NCTC 135, Ultra DOMA PF or HL-1 (both from Biowhittaker; Walkersville, Md.), may be used.

The medium can be supplemented with a variety of growth factors, cytokines, serum, etc., depending on the cells being cultured. Examples of suitable growth factors include: basic fibroblast growth factor (bFGF), vascular endothelial growth factor (VEGF), epidermal growth factor (EGF), transforming growth factors (TGFα and TGFβ), platelet derived growth factors (PDGFs), hepatocyte growth factor (HGF), insulin-like growth factor (IGF), insulin, erythropoietin (EPO), and colony stimulating factor (CSF). Examples of suitable hormone additives are estrogen, progesterone, testosterone or glucocorticoids such as dexamethasone. Examples of cytokine medium additives are interferons, interleukins or tumor necrosis factor-α (TNFα). Salt solutions may also be added to the media, including Alseverr's Solution, Dulbecco's Phosphate Buffered Saline (DPBS), Earle's Balanced Salt Solution, Gey's Balanced Salt Solution (GBSS), Hanks' Balanced Salt Solution (HBSS), Puck's Saline A, and Tyrode's Salt Solution. If necessary, additives and culture components in different culture conditions be can optimized, as these may alter cell response, activity lifetime or other features affecting bioactivity. In addition, the surface on which the cells are grown can be coated with a variety of substrates that contribute to survival, growth and/or differentiation of the cells. These substrates include but are not limited to, laminin, EHS-matrix, collagens, poly-L-lysine, poly-D-lysine, polyomithine and fibronectin. When three-dimensional cultures are desired, extracellular matrix gels may be used, such as collagen, EHS-matrix, or gelatin (denatured collagen). Cells may be grown on top of such matrices, or may be cast within the gels themselves.

If desired, the media may be further supplemented with reagents that limit acidosis of the cultures, such as buffer addition to the medium (such as N,N-bis(2-hydroxyethyl)-2-aminoethanesulfonic acid (BES), bis(2-hydroxyethyl)amino-tris(hydroxymethyl)methane (BIS-Tris), N-(20hydroxyethyl)piperazine-N'3-propanesulfonic acid (EPPS or HEPPS), glyclclycine, N-2-hydroxyehtylpiperazine-N'-2-ethanesulfonic acid (HEPES), 3-(N-morpholino)propane sulfonic acid (MOPS), Piperazine-N,N'-bis(2-ethane-sulfonic acid)(PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Frequent medium changes and changes in the supplied $CO_2$ (often approximately 5%) concentration may also be used to control acidosis.

Gases for culture typically are about 5% carbon dioxide and the remainder nitrogen, but optionally may contain varying mounts of nitric oxide (starting as low as 3 ppm), carbon monoxide and other gases, both inert and biologically active. Carbon dioxide concentrations typically range around 5%, but may vary between 2-10%. Both nitric oxide and carbon monoxide, when necessary, are typically administered in very small amounts (i.e. in the ppm range), determined empirically or from the literature. The temperature at which the cells will grow optimally can be empirically determined, although the culture temperature will usually be within the normal physiological range of the animal from which the cells were isolated.

Detecting Nucleolin: Antibody-Based Methods

Nucleolin can be detected at the protein level in cells, tissue sections, cultured cells and extracts thereof. Immunochemical methods to detect protein expression are well known and include, but are not limited to, Western blotting, immunoaffinity purification, immunoprecipitation, enzyme-linked immunosorbent assay (ELISA), dot or slot blotting, radioimmunoassay (RIA), immunohistochemical detection, immunocytochemical staining, and flow cytometry. Common procedures and instructions using antibodies have been well addressed (e.g., Harlow and Lane, 1988; Harlow and Lane, 1999). Selected antibodies that are useful for detecting plasma membrane nucleolin are shown in Table 1.

TABLE 1

Anti-nucleolin antibodies

| Antibody | Source | Antigen source | Notes |
| --- | --- | --- | --- |
| p7-1A4 mouse monoclonal antibody (mAb) | Developmental Studies Hybridoma Bank (University of Iowa; Ames, IA) | Xenopus laevis oocytes | IgG$_1$ |
| sc-8031 mouse mAb | Santa Cruz Biotech (Santa Cruz, CA) | human | IgG$_1$ |
| sc-9893 goat polyclonal Ab (pAb) | Santa Cruz Biotech | human | IgG |
| sc-9892 goat pAb | Santa Cruz Biotech | human | IgG |
| clone 4E2 mouse mAb | MBL International (Watertown, MA) | human | IgG$_1$ |

TABLE 1-continued

Anti-nucleolin antibodies

| Antibody | Source | Antigen source | Notes |
|---|---|---|---|
| clone 3G4B2 mouse mAb | Upstate Biotechnology (Lake Placid, NY) | dog (MDCK cells) | $IgG_{1k}$ |

If additional anti-plasma membrane nucleolin antibodies are desired, they can be produced using well-known methods (Harlow and Lane, 1988; Harlow and Lane, 1999). For example, (pAbs) can be raised in a mammalian host by one or more injections of an immunogen, such as an extracellular domain of surface-expressed nucleolin, and, if desired, an adjuvant. Typically, the immunogen (and adjuvant) is injected in a mammal by a subcutaneous or intraperitoneal injection. The immunogen may include components such as polypeptides (isolated, non-isolated, or recombinantly produced), cells or cell fractions. Examples of adjuvants include Freund's complete and monophosphoryl Lipid A synthetic-trehalose dicorynomycolate (MPL-TDM). To improve the immune response, an immunogen may be conjugated to a polypeptide that is immunogenic in the host, such as keyhole limpet hemocyanin (KLH), serum albumin, bovine thyroglobulin or soybean trypsin inhibitor. Alternatively, pAbs may be made in chickens, producing IgY molecules (Schade et. al., 1996).

mAbs may also be made by immunizing a host or lymphocytes from a host, harvesting the mAb-secreting (or potentially secreting) lymphocytes, fusing those lymphocytes to immortalized cells (e.g., myeloma cells), and selecting those cells that secrete the desired mAb (Goding, 1996). If desired, the mAbs may be purified from the culture medium or ascites fluid by conventional procedures such as protein A-sepharose, hydroxylapatite chromatography, gel electrophoresis, dialysis, ammonium sulfate precipitation or affinity chromatography (Harlow and Lane, 1988; Harlow and Lane, 1999).

The antibodies may be whole antibodies and fragments or derivatives thereof. For example, when assaying live cells, using $F_{ab}$ fragments will eliminate cross-linking, thus preventing the cells from endocytosing the bound antibodies.

An approach using antibodies to detect the presence of an antigen will include one or more, if not all, of the following steps:

(1) Preparing the entity being tested for plasma membrane nucleolin by washing with buffer or water
(2) Blocking non-specific antibody binding sites
(3) Applying the antibody (e.g., nucleolin)
(4) Detecting bound antibody, either via a detectable labeled-secondary antibody that recognizes the primary antibody or a detectable label that has been directly attached to, or associated with, the bound (anti-nucleolin) antibody.

Substrates may be washed with any solution that does not interfere with the epitope structure. Common buffers include saline and biological buffers, such as bicine, tricine, and Tris.

Non-specific binding sites are blocked by applying a protein solution, such as bovine serum albumin (BSA; denatured or native), milk proteins, or in the cases wherein the detecting reagent is a secondary antibody, normal serum or immunoglobulins from a non-immunized host animal whose species is the same origin as the detecting antibody. For example, a procedure using a secondary antibody made in goats would employ normal goat serum (NGS).

The substrate is then reacted with the antibody of interest. The antibody may be applied in any form, such as $F_{ab}$ fragments and derivatives thereof, purified antibody (by affinity, precipitation, etc.), supernatant from hybridoma cultures, ascites, serum or recombinant antibodies expressed in recombinant cells. The antibody may be diluted in buffer or media, often with a protein carrier such as the solution used to block non-specific binding sites; the useful antibody concentration is usually determined empirically. In general, polyclonal sera, purified antibodies and ascites may be diluted 1:50 to 1:200,000, more often, 1:200 to 1:500. Hybridoma supernatants may be diluted 1:0 to 1:10, or may be concentrated by dialysis or ammonium sulfate precipitation (or any other method that retains the antibodies of interest but at least partially removes the liquid component and preferably other small molecules, such as salts) and diluted if necessary. Incubation with antibodies may be carried out for as little as 20 minutes at 37° C., 2 to 6 hours at room temperature (approximately 22° C.), or 8 hours or more at 4° C.

To detect an antibody-antigen complex, a label may be used. The label may be coupled to the binding antibody, or to a second antibody that recognizes the first antibody, and is incubated with the sample after the primary antibody incubation and thorough washing. Suitable labels include fluorescent moieties, such as fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3 and 5; phycoerythrin; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives; pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diaza-s-indacene. Suitable labels further include enzymatic moieties, such as alkaline phosphatase or horseradish peroxidase; radioactive moieties, including $^{35}S$ and $^{135}I$-labels; avidin (or streptavidin)-biotin-based detection systems (often coupled with enzymatic or gold signal systems); and gold particles. In the case of enzymatic-based detection systems, the enzyme is reacted with an appropriate substrate, such as 3, 3'-diaminobenzidine (DAB) for horseradish peroxidase; preferably, the reaction products are insoluble. Gold-labeled samples, if not prepared for ultrastructural analyses, may be chemically reacted to enhance the gold signal; this approach is especially desirable for light microscopy. The choice of the label depends on the application, the desired resolution and the desired observation methods. For fluorescent labels, the fluorophore is excited with the appropriate wavelength and the sample observed using a microscope, confocal microscope, or FACS machine. In the case of radioactive labeling, the samples are contacted with autoradiography film, and the film developed; alternatively, autoradiography may also be accomplished using ultrastructural approaches. Alternatively, radioactivity may be quantified using a scintillation counter.

Cytological-Based Approaches:

Immunofluorescence/Immunohistochemical

Protein expression by cells or tissue can be ascertained by immunolocalization of an antigen. Generally, cells or tissue are preserved by fixation, exposed to an antibody that recognizes the epitope of interest, such as a nucleolin, and the bound antibody visualized.

Any cell, cell line, tissue, or even an entire organism is appropriate for fixation. Cells may be cultured in vitro as primary cultures, cell lines, or harvested from tissue and separated mechanically or enzymatically. Tissue may be from any organ, plant or animal, and may be harvested after or prior to fixation. Fixation, if desired, may be by any known means; the requirements are that the protein to be detected be not rendered unrecognizable by the binding agent, most often an antibody. Appropriate fixatives include paraformaldehyde-lysine-periodate, formalin, paraformaldehyde, methanol, acetic acid-methanol, glutaraldehyde, acetone, Karnovsky's fixative, etc. The choice of fixative depends on variables such as the protein of interest, the properties of a particular detecting reagent (such as an antibody), the method of detection (fluorescence, enzymatic) and the method of observation (epifluorescence microscopy, confocal microscopy, light microscopy, electron microscopy, etc.). The sample is usually first washed, most often with a biological buffer, prior to fixation. Fixatives are prepared in solution or in biological buffers; many fixatives are prepared immediately prior to applying to the sample. Suitable biological buffers include saline (e.g., phosphate buffered saline), N-(carbamoylmethyl)-2-aminoethanesulfonic acid (ACES), N-2-acetamido-2-iminodiacetic acid (ADA), bicine, bis-tris, 3-cyclohexylamino-2-hydroxy-1-propanesulfonic acid (CAPSO), ethanolamines, glycine, N-2-hydroxyethylpiperazine-N'-2-ethanesulfonic acid (HEPES), 2-N-morpholinoethanesulfonic acid (MES), 3-N-morpholinopropanesulfonic acid (MOPS), 3-N-morpholino-2-hydroxy-propanesulfonic acid (MOPSO), piperazine-N,N'-bis(2-ethanesulfonic acid) (PIPES), tricine, triethanolamine, etc. An appropriate buffer is selected according to the sample being analyzed, appropriate pH, and the requirements of the detection method. A useful buffer is phosphate buffered saline (PBS). After fixation, the sample may be stored in fixative, preferably fresh, or temporarily or indefinitely, at a temperature between about 4° C. to about 22° C.

After fixation from 5 minutes to 1 week, depending on the sample size, sample thickness, and viscosity of the fixative, the sample is washed in buffer. If the sample is thick or sections are desired, the sample may be embedded in a suitable matrix. For cryosectioning, sucrose is infused, and embedded in a matrix, such as OCT Tissue Tek (Andwin Scientific; Canoga Park, Calif.) or gelatin. Samples may also be embedded in paraffin wax, or resins suitable for electron microscopy, such as epoxy-based (Araldite, Polybed 812, Durcupan ACM, Quetol, Spurr's, or mixtures thereof; Polysciences, Warrington, Pa.), acrylates (London Resins (LR White, LR gold), Lowicryls, Unicryl; Polysciences), methylacrylates (JB-4, OsteoBed; Polysciences), melamine (Nanoplast; Polysciences) and other media, such as DGD, Immuno-Bed (Polysciences) and then polymerized. Resins that are especially appropriate include hydrophilic (such as Lowicryls, London Resins, water-soluble Durcupan, etc.) since these are less likely to denature the protein of interest during polymerization and will not repel antibody solutions. When embedded in wax or resin, samples are dehydrated by passing them through a concentration series of ethanol or methanol; in some cases, other solvents may be used, such as polypropylene oxide. Embedding may occur after the sample has been reacted with the detecting agents, or samples may be first embedded, sectioned (via microtome, cyrotome, or ultramicrotome), and then the sections reacted with the detecting reagents. In some cases, the embedding material may be partially or completely removed before detection to facilitate antigen access.

In some instances, the nucleolin epitope(s) to which the antibody binds may be rendered unavailable because of fixation. Antigen retrieval methods can be used to make the antigen available for antibody binding. Many recourses are available (reviewed in, for example, McNicol and Richmond, 1998; Robinson and Vandre, 2001; Shi et al., 2001). Common methods include using heat supplied from autoclaves, microwaves, hot water or buffers, pressure cookers, or other sources of heat. Often the sources of heat are used in sequence; the samples must often be in solution (e.g., microwave treatments). Detergent treatment may also unmask antigens, such as sodium dodecyl sulfate (SDS, 0.25% to 1%) or other denaturing detergents. Chemical methods include strong alkalis (such as NaOH), prolonged immersion in water, urea, formic acid and refixation in zinc sulfate-formalin. In other instances, proteolytic enzyme treatment will modify the antigen such that it is available to the antibody. Any number of proteases may be used, such as trypsin. These methods may be combined to achieve optimal results. The choice of the antigen retrieval method will depend on the sample, its embedment (if any), and the anti-nucleolin antibody.

Especially in the cases of immunofluorescent or enzymatic product-based detection, background signal due to residual fixative, protein cross-linking, protein precipitation or endogenous enzymes may be quenched, using, e.g., ammonium chloride or sodium borohydride or a substance to deactivate or deplete confounding endogenous enzymes, such as hydrogen peroxide which acts on peroxidases. To detect intracellular proteins in samples that are not to be sectioned, samples may be permeabilized. Permeabilizing agents include detergents, such as t-octylphenoxypolyethoxyethanols, polyoxyethylenesorbitans, and other agents, such as lysins, proteases, etc.

Non-specific binding sites are blocked by applying a protein solution, such as bovine serum albumin (BSA; denatured or native), milk proteins, or preferably in the cases wherein the detecting reagent is an antibody, normal serum or IgG from a non-immunized host animal whose species is the same is the same origin of the detecting antibody.

Flow Cytometry/Fluorescence-Activated Cell Sorting (FACS)

Methods of performing flow cytometry are well known (Orfao and Ruiz-Arguelles, 1996). Because plasma membrane nucleolin is being probed, cell permeabilization that allows access to cytoplasmic compartments is undesirable. After harvesting, cells are prepared as a single-cell suspension; cells are then incubated with an anti-nucleolin antibody usually after blocking non-specific binding sites. Preferably, the anti-nucleolin antibody is labeled with a fluorescent marker. If the antibody is not labeled with a fluorescent marker, a second antibody that is immunoreactive with the first antibody and contains a fluorescent marker is used. After sufficient washing to ensure that excess or unbound antibodies are removed, the cells are ready for flow cytometry.

Biochemical-Based Approaches:

In these approaches, it is first desirable to isolate plasma membrane proteins from other cellular compartments. This may be done in any number of ways, such as simple cell extraction, differential extraction or mechanical disruption followed by separation of cellular compartments on gradients (such as sucrose or polydextran) by centrifugation, extraction followed by immunoselecting appropriate cellular compartments with plasma membrane-specific antibodies, etc. An example of such an approach is described in Naito et al. (1988) and Yao et al. (1996b). Extracting reagents are well known. For examples, solvents such as methanol may be occasionally useful. More likely, detergents, such as t-octylphenoxypolyethoxyethanol (also known as polyethylene glycol tert-octylphenyl ether) are particularly useful for simple extractions. Also useful are glucopyranosides, maltopyranosides, maltosides, polyoxyethylene esters, other polyoxyethylene ethers, salts of alginic, caprylic, cholic 1-decanesulfonic, deoxycholic, dioctyl sulfosuccinate, 1-dodecanesulfonic, glyocholic, glycodeoxycholic, 1-heptanesulfonic, 1-hexanesulfonic, N-lauroylsacrosine, lauryl sulfate (e.g., SDS), 1-nonanesulfonic, 1-octanesulfonic, 1-pentanesulfonic, taurocholic and tauodexycholic acids; sodium 7-ethyl-2-methyl-4-undecyl sulfate, and sodium 2-ethylhexyl sulfate. Other useful detergents include(3-[(3-cholamidopropyl)dimethylammonio]-1-propane-sulfonate, (3-[(3-cholamidopropyl)dimethylammonio]-2-hydroxy-1-propane-sulfonate, N-decyl-, N-dodecyl-, N-hexadecyl-, N-octadecyl-, N-tetradecyl-N,N-dimethyl-3-ammonio-1-propanesulfonates and phosphatidylcholine. Less useful, but may be helpful in some cases, are alkyltrimethylammonium bromides, benzalkonium chloride, benzethonium chloride, benzyldimethyldodecylammonium bromide, benzyldimethylhexadecylammonium chloride, cetyldimethylethylammonium bromide, cetylpyridinium, decamethonium bormide, dimethyldioctadecylammonium bromide, methylbenzethonium chloride, methyltiroctylammonium chloride, and N,N', N'-polyoxyehtlylene(10)-N-tallow-1,3-diaminopropane.
The different extracting reagents may be used singly or in combination; they may be prepared in simple aqueous solutions or suitable buffers.

Polyethylene glycol ter-octylphenyl ether is particularly useful for differential extraction by taking advantage of the low cloud point to separate membrane proteins from soluble proteins into two different phases.

Extraction buffers may contain protease inhibitors, such as aprotinin, benzamidine, antipain, pepstatin and iodoacetamide.

Extracts are then assayed for nucleolin expression. For those techniques that separate surface plasma membrane from other cellular components (especially the nucleus), the nucleolin detecting agents need not be specific for extracellular plasma membrane nucleolin epitopes.

Immunosorbent Assay (ELISA)(Ausubel et al. 1987)

Various types of enzyme linked immunosorbent assays (ELISAs) to detect protein expression are known, and these are applicable to nucleolin detection. However, other ELISA-like assays include radio-immunoassays and other non-enzyme linked antibody binding assays and procedures. In these assays, the cell surface proteins are the principle components in the cell preparation.

The double antibody-sandwich ELISA technique is especially useful. The basic protocol for a double antibody-sandwich ELISA is as follows: A plate is coated with anti-nucleolin antibodies (capture antibodies). The plate is then washed with a blocking agent, such as BSA, to block non-specific binding of proteins (antibodies or antigens) to the test plate. The test sample is then incubated on the plate coated with the capture antibodies. The plate is then washed, incubated with anti-nucleolin antibodies, washed again, and incubated with a specific antibody-labeled conjugates and the signal appropriately detected.

In other ELISAs, proteins or peptides are immobilized onto a selected surface, the surface exhibit may have affinity for proteins, such as the wells of a specially-treated polystyrene microtiter plate. After washing to remove incompletely adsorbed material, one would then generally desire to bind or coat with a nonspecific protein that is known to be antigenically neutral with anti-nucleolin antibodies, such as BSA or casein, onto the well bottom. This step allows for blocking of nonspecific adsorption sites on the immobilizing surface and thus reduces the background caused by nonspecific binding of antibodies onto the surface. When the antibodies were created in an animal by conjugating a polypeptide to a protein (e.g., BSA), a different protein is usually used as a blocking agent, because of the possibility of the presence of antibodies to the blocking protein the antibody composition.

After binding of nucleolin to the well, coating with a non-reactive material to reduce background, and washing to remove unbound material, the immobilizing surface is contacted with an anti-nucleolin antibody composition in a manner conducive to immune complex (antigen/antibody) formation. Such conditions include diluting the antibody composition with diluents such as BSA, bovine γ globulin (BGG) and PBS/Polyoxyethylenesorbitan monolaurate. These added agents also assist in the reduction of nonspecific background signal. The layered antibody composition is then allowed to incubate for, e.g., from 2 to 4 hours at 25° C. to 37° C. Following incubation, the antibody composition-contacted surface is washed so as to remove non-immunocomplexed material. One washing procedure includes washing with a PBS/polyoxyethylenesorbitan monolaurate or borate buffer solution.

Following formation of specific immunocomplexes between the test sample and the antibody and subsequent washing, immunocomplex formation is detected using a second antibody having specificity for the anti-nucleolin antibody. For detection, the secondary antibody is associated with detectable label, such as an enzyme or a fluorescent molecule. A number of immunoassays are discussed in U.S. Pat. Nos. 5,736,348, 5,192,660, and 4,474,892.

Western Blotting (Ausubel et al., 1987)

Western blotting methods are well known. Generally, a protein sample is subjected to sodium dodecyl sulfate-polyacrylamide gel electrophoresis (SDS-PAGE) at such conditions as to yield an appropriate separation of proteins within the sample. The proteins are then transferred to a membrane (e.g., nitrocellulose, nylon, etc.) in such a way as to maintain the relative positions of the proteins to each other.

Visibly labeled proteins of known molecular weight may be included within a lane of the gel. These proteins serve as a control to insure adequate transfer of the proteins to the membrane, as well as molecular weight markers for determining the relative molecular weight of other proteins on the blot. Alternatively, unlabeled marker proteins (or in some rare instances, no marker proteins) are detected after transfer with Brilliant Blue (G or R; Sigma; St. Louis, Mo.) other protein dyes. After protein transfer, the membrane is submersed in a blocking solution to prevent nonspecific binding of the primary antibody.

The primary antibody, e.g., anti-nucleolin, may be labeled and the presence and molecular weight of the antigen may be determined by detecting the label at a specific location on the membrane. However, the primary antibody may not be labeled, and the blot is further reacted with a labeled second antibody. This secondary antibody is immunoreactive with the primary antibody; for example, the secondary antibody may be one to rabbit imunoglobulins and labeled with alkaline phosphatase. An apparatus for and methods of performing Western blots are described in U.S. Pat. No. 5,567,595.

Immunoprecipitation (Ausubel et al., 1987: Harlow and Lane, 1999)

Protein expression can be determined and quantified by isolating antigens using immunoprecipitation. Methods of immunoprecipitations are described in U.S. Pat. No. 5,629,197. Immunoprecipitation involves the separation of the target antigen component from a complex mixture and is used to discriminate or isolate minute amounts of protein. For the isolation of cell-surface proteins, nonionic salts are often used.

For example, an immunoprecipitation from whole cells may be performed as follows. Cells are extracted with one or more detergents (see above), such as, for example, 1% t-octylphenoxypolyethoxyethanol/0.1% SDS/150 mM NaCl in 20 mM Tris buffer, pH 8.6. After extraction, which may be aided by agitation, insoluble debris is removed using a centrifuge. Anti-nucleolin antibody is added to the extracts, and then the samples are incubated 30 minutes to overnight at 4° C. *Staphylococcus aureus* or recombinantly-produced Protein A or Group C *Staphylococcus* Protein G conjugated to sepharose or tris-acryl beads are then added. In those instances when the anti-nucleolin antibody does not bind well to Protein A, IgG Abs that recognize antibodies of the animal in which the anti-nucleolin antibody was made is simultaneously added. The samples are then incubated with gentle agitation for around 2 hours at 4° C. The beads or bacterial cells, now bound to the antibody-antigen complexes, are thoroughly washed, usually first with either the extraction solution or a high salt buffer, then a salt-less buffer or water to remove nonspecifically-bound proteins and residual detergent molecules. After removing residual buffer, the beads are incubated with a buffer, such as electrophoresis sample buffer, and then subjected to 95° C. for 3-5 minutes to elute bound proteins from the beads. The samples are then ready for analysis and nucleolin detection.

Other Methods:

Immunoselection Procedures (other than FACS)(Ausubel et al., 1987)

Cells expressing plasma membrane nucleolin can be easily isolated by "panning" on plastic plates coated with anti-antibody antibodies (Wysocki and Sato, 1978). Panning has many advantages over other immunoselection procedures: It is fast, efficient ($10^7$ cells can easily be panned on two 60-mm plastic plates in 30 minutes), and inexpensive.

In general, a single cell suspension is labeled with an anti-nucleolin antibody, and then is incubated on a substrate coated with a secondary antibody (with nonspecific binding sites blocked). After 1 to 3 hours incubation at room temperature, non-adherent cells are washed away. In this embodiment, bound cells indicate that nucleolin is expressed in the plasma membrane, indicating a neoplastic cell.

Detecting Nucleolin: Oligonucleotide-Based Methods

GROs and other oligonucleotides that recognize and bind nucleolin (Bates et al., 1999; Miller et al., WO 00/61597, 2000; Xu et al., 2001) can be used much the same way as antibodies are. Examples of suitable assays are given below. In some cases, incorporating the GRO nucleotides into larger nucleic acid sequences may be advantageous; for example, to facilitate binding of a GRO nucleic acid to a substrate without denaturing the nucleolin-binding site.

Useful GROs that bind nucleolin (and also have the biological property of inhibiting cancer cell growth) have been described (Bates et al., 1999; Miller et al., WO 00/61597, 2000; Xu et al., 2001). They include those shown in Table 2. Control GROs are useful for detecting background signal levels.

TABLE 2

Non-antisense GRO that bind nucleolin and non-binding controls[1,2,3]

| GRO | Sequence | SEQ ID NO: |
|---|---|---|
| GRO29A[1] | tttggtggtg gtggttgtgg tggtggtgg | 1 |
| GRO29-2 | tttggtggtg gtggttttgg tggtggtgg | 2 |
| GRO29-3 | tttggtggtg gtggtggtgg tggtggtgg | 3 |
| GRO29-5 | tttggtggtg gtggttttgg tggtggtgg | 4 |
| GRO29-13 | tggtggtggt ggt | 5 |
| GRO14C | ggtggttgtg gtgg | 6 |
| GRO15A | gttgtttggg gtggt | 7 |
| GRO15B[2] | ttgggggggg tgggt | 8 |
| GRO25A | ggttggggtg ggtggggtgg gtggg | 9 |
| GRO26B[1] | ggtggtggtg gttgtggtgg tggtgg | 10 |
| GRO28A | tttggtggtg gtggttgtgg tggtggtg | 11 |
| GRO28B | tttggtggtg gtggtgtggt ggtggtgg | 12 |
| GRO29-6 | ggtggtggtg gttgtggtgg tggtggttt | 13 |
| GRO32A | ggtggttgtg gtggttgtgg tggttgtggt gg | 14 |
| GRO32B | tttggtggtg gtggttgtgg tggtggtggt tt | 15 |
| GRO56A | ggtggtggtg gttgtggtgg tggtggttgt ggtggtggtg gttgtggtgg tggtgg | 16 |
| CRO | tttcctcctc ctccttctcc tcctcctcc | 18 |
| GRO A | ttagggttag ggttagggtt aggg | 19 |
| GRO B | ggtggtggtg g | 20 |
| GRO C | ggtggttgtg gtgg | 21 |
| GRO D | ggttggtgtg gttgg | 22 |
| GRO E | gggttttggg | 23 |
| GRO F | ggttttggtt ttggttttgg | 24 |
| GRO G[1] | ggttggtgtg gttgg | 25 |
| GRO H[1] | ggggttttgg gg | 26 |
| GRO I[1] | gggttttggg | 27 |
| GRO J[1] | ggggttttgg ggttttgggg ttttgggg | 28 |
| GRO K[1] | ttggggttgg ggttgggggtt gggg | 29 |
| GRO L[1] | gggtgggtgg gtgggt | 30 |
| GRO M[1] | ggttttggtt ttggttttgg ttttgg | 31 |
| GRO N[2] | tttcctcctc ctccttctcc tcctcctcc | 32 |
| GRO O[2] | cctcctcctc cttctcctcc tcctcc | 33 |
| GRO P[2] | tggggt | 34 |
| GRO Q[2] | gcatgct | 35 |

TABLE 2-continued

Non-antisense GRO that bind nucleolin and non-binding controls[1,2,3]

| GRO | Sequence | SEQ ID NO: |
|---|---|---|
| GRO R[2] | gcggtttgcg g | 36 |
| GRO S[2] | tagg | 37 |
| GRO T[2] | ggggttgggg tgtggggttg ggg | 38 |

[1]Indicates a good plasma membrane nucleolin-binding GRO. [2]Indicates a nucleolin control (non-plasma membrane nucleolin binding). [3]GRO sequence without [1] or [2] designations have some anti-proliferative activity.

Cytological-Based Approaches:

Cellular Localization/Labeling (Relative of Immuno-Based Localization/Labeling Assays)

The procedures outlined above for the immuno-based localization assays (such as immunofluorescence or FACS) are also applicable to those assays wherein the detecting reagent is a nucleolin-binding GRO. Modifications include those to prevent non-specific binding, using denatured DNA, such as from salmon sperm instead of a protein such as BSA. For detection, similar labels as outlined above are also useful as long as the GRO can be derivatized with the label in some form. For this purpose, biotin-avidin nucleic acid labeling systems are especially convenient, as are digoxigenin ones (Ausubel et al., 1987). The synthesis of biotinylated nucleotides has been described (Langer et al., 1981). Biotin, a water-soluble vitamin, can covalently attached to the C5 position of the pyrimidine ring via an alylamine linker arm; biotin non-covalently binds avidin or streptavidin, which may be easily labeled. Alternatively, biotin is added to oligonucleotides during synthesis by coupling to the 5'-hydroxyl of the terminal nucleotide. Digoxigenin-11-dUTP can be incorporated into DNA by either nick translation or random oligonucleotide-primed synthesis protocols. Digoxigenin is detected using labeled anti-digoxigenin antibodies. Convenient digoxigenin systems are commercially available (Roche Molecular Biochemicals; Indianapolis, Ind.). An example of a procedure using oligonucleotides to detect and localize proteins has been described by Davis et al., 1998.

Biochemical-Based Approaches:

GROs may also be used in a similar fashion as antibodies to detect nucleolin in biochemical approaches, as described above. For example, "Southwestern"-type blotting experiments may be performed with GROs (Bates et al., 1999; Miller et al., WO 00/61597, 2000). After cells have been appropriately extracted (for example, differentially to separate plasma membrane proteins from intracellular proteins), the proteins are subjected to electrophoresis on polyacrylamide gels and transferred to a substrate, such as a polyvinliden difluoride membrane. Proteins are denatured and renatured by washing for 30 minutes at 4° C. with 6 M gaunidine-HCl, followed by washes in 3 M, 1.5 M and 0.75 M guanidine HCl in 25 mM HEPES (pH 7.9)/4 mM KCl/3 mM $MgCl_2$). After blocking non-specific binding sites with 5% non-fat dried milk in HEPES buffer, the labeled GRO is hybridized for 2 hours at 4° C. in HEPES binding buffer supplemented with 0.25% NDM, 0.05% NP-40, 400 ng/ml salmon sperm DNA and 100 ng/ml of an unrelated mixed sequence oligonucleotide, such as tcgagaaaaa ctctcctctc cttccttcct ctcca; SEQ ID NO:17. After washing with HEPES binding buffer, the signal is detected appropriately.

Other Methods:

Arrays

Arrays of Immobilized Nucleolin-Binding Reagents on Chips

A chip is an array of regions containing immobilized molecules, separated by regions containing no molecules or immobilized molecules at a much lower density. For example, a protein chip may be prepared by applying nucleolin-binding antibodies; an "aptamer"-like chip may be prepared by applying nucleolin binding GROs. The remaining regions are left uncovered or are covered with inert molecules. The arrays can be rinsed to remove all but the specifically immobilized polypeptides or nucleic acids. In addition, chips may also be prepared containing multiple nucleolin-binding antibodies (Table 1), nucleic acids (such as GROs; Table 2), or both, and may contain control antibodies and/or nucleic acids that are non-reactive with nucleolin. Such an array would allow for simultaneous test confirmation, duplication and internal controls.

Proteins, such as anti-nucleolin antibodies, can be immobilized onto solid supports by simple chemical reactions, including the condensation of amines with carboxylic acids and the formation of disulfides. This covalent immobilization of proteins on inert substrates can prevent high background signals due to non-specific adsorption. Substrates derivatized with other molecules, such as biotin, are also useful when the protein to be immobilized is derivatized with avidin or streptavidin, or vice-versa. In some rare cases, especially when anti-nucleolin antibody-encoding nucleic acid sequences are available, fusion polypeptides comprising anti-nucleolin antibody may be advantageous for immobilization onto a substrate.

The surface may be any material to which a the nucleolin binding agent can be immobilized. For example, the surface may be metal, glass, ceramic, polymer, wood or biological tissue. The surface may include a substrate of a given material and a layer or layers of another material on a portion or the entire surface of the substrate.

The surfaces may be any of the common surfaces used for affinity chromatography, such as those used for immobilization of glutathione for the purification of GST fusion polypeptides. The surfaces for affinity chromatography include, for example, sepharose, agarose, polyacrylamide, polystyrene and dextran. The surface need not be a solid, but may be a colloid, an exfoliated mineral clay, a lipid monolayer, a lipid bilayer, a gel, or a porous material.

The immobilization method desirably controls the position of the nucleolin binding agent on the surface; for example, enabling the antigen binding portions of antibodies unattached to the substrate, while the non-antigen binding portions are rooted to the substrate. By controlling the position of individual reactant ligands, patterns or arrays of the ligands may be produced. The portions of the surface that are not occupied by the nucleolin-binding reagent do not allow non-specific adsorption of polypeptides or polynucleotides. In this embodiment, a sample from a subject, for example, blood, is passed over a chip containing nucleolin-binding molecules. A biosensing device, such as machine that detects changes in surface plasmon resonance, is then used to detect bound nucleolin. BIAcore (Uppsala, Sweden) chips serve as examples of useful chips and detection machines.

Prognostic Assays

Diagnostic methods can furthermore be used to identify subjects having, or at risk of developing, a neoplasia at an early stage of disease development, since the surface expression of nucleolin can be detected earlier than in conventional methods. Prognostic assays can be used to identify a subject having or at risk for developing a neoplasia, such as a subject who has a family history of harmful neoplasias, especially cancers. A method for identifying such an individual would include a test sample obtained from a subject and testing for cell surface localization of nucleolin.

In another embodiment, detecting plasma membrane nucleolin and then either qualitatively or quantitatively assessing the amount of nucleolin (usually indirectly through the signal generated from bound nucleolin molecules) can indicate the rate of cell proliferation, since plasma membrane nucleolin levels correlate with cell proliferation rates.

Kits

Kits, containers, packs, or dispensers containing nucleolin probes and detection reagents, together with instructions for administration, may be assembled. When supplied as a kit, the different components may be packaged in separate containers and admixed immediately before use. Such packaging of the components separately may permit long-term storage without losing the active components' functions.

Kits may also include reagents in separate containers that facilitate the execution of a specific test, such as diagnostic tests. For example, non-nucleolin-binding GROs may be supplied for internal negative controls, or nucleolin and a nucleolin-binding reagent for internal positive controls. The components of a kit are an anti-nucleolin agent used to probe for nucleolin, a control sample, and optionally a composition to detect nucleolin. Examples of anti-nucleolin agents include an anti-nucleolin antibody (e.g., as shown in Table 1) or fragment thereof; if labeled, then a nucleolin-binding detection reagent is superfluous. A nucleolin-binding oligonucleotide (e.g., as shown in Table 2), which may be derivatized such that a second labeled reagent may bind (such as biotin). However, if a labeled GRO nucleic acid is provided, then a second labeled reagent is superfluous. Examples of detection reagents include: labeled secondary antibodies, for example, an anti-mouse pAb made in donkey and then tagged with a fluorophore such as rhodamine, or a labeled reagent to detect oligonucleotides such as GROs; for example, avidin or streptavidin linked to horseradish peroxidase when the probe is biotinylated. Control components may include: normal serum from the animal in which a secondary antibody was made; a solution containing nucleolin polypeptide or nucleolin binding oligonucleotide; a dot blot of nucleolin protein to assay nucleolin-binding reagent reactivity; or fixed or preserved cells that express nucleolin in the plasma membrane. Other components may include buffers, fixatives, blocking solutions, microscope slides and/or cover slips or other suitable substrates for analysis, such as microtiter plates; detergent or detergent solutions or other cell extraction reagents; miscellaneous reagents, protease inhibitors, various containers and miscellaneous tools and equipment to facilitate the assays.

(a) Containers or Vessels

The reagents included in the kits can be supplied in containers of any sort such that the life of the different components are preserved and are not adsorbed or altered by the materials of the container. For example, sealed glass ampules may contain lyophilized nucleolin binding reagents (such as anti-nucleolin antibodies or nucleolin-binding oligonucleotides) or buffers that have been packaged under a neutral, non-reacting gas, such as nitrogen. Ampules may consist of any suitable material, such as glass, organic polymers (i.e., polycarbonate, polystyrene, etc.), ceramic, metal or any other material typically employed to hold reagents. Other examples of suitable containers include simple bottles that may be fabricated from similar substances as ampules, and envelopes that may have foil-lined interiors, such as aluminum or alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional Materials

Kits may also be supplied with instructional materials. Instructions may be printed on paper or other substrate and/or may be supplied as an electronic-readable medium, such as a floppy disc, CD-ROM, DVD-ROM, DVD, videotape, audio tape, etc. Detailed instructions may not be physically associated with the kit; instead, a user may be directed to an internet web site specified by the manufacturer or distributor of the kit, or supplied as electronic mail.

The following examples are intended to illustrate the present invention without limitation.

EXAMPLES

Example 1

Immunofluorescent Labeling of Plasma Membrane Nucleolin in Cells

This example illustrates a procedure that stains nuclear nucleolin, or only plasma membrane nucleolin.

Cells from the cell lines DU145 (human prostrate cancer), MDA-MB-231 (human breast cancer) HeLa (human cervical cancer) and HS27 (normal skin fibroblasts)(all available from ATCC; Manassas, Va.) were released from culture substrates with trypsin, resuspended into single cells and plated onto microscope slides. The slides seeded with cells were incubated at 37° C. until they were well attached, as assayed by visual inspection using a microscope. After rinsing the attached cells once with PBS for two minutes, they were fixed in 4% formaldehyde/PBS for at least 15 minutes at 22° C. For nuclear nucleolin staining, cells are permeabilized with 1% Triton X-100 prior to contacting with antibody. After washing twice with PBS, 5 minutes/wash, non-specific binding sites were blocked for 15-60 minutes with 1% NGS/PBS at 22° C., and then incubated with mouse anti-nucleolin antibodies diluted in 1% NGS/PBS or PBS/Tween (0.05%-0.1%) for 1 hour to overnight at 4° C. The samples were washed four times, 5 minutes each with PBS, and then incubated with goat anti-mouse pAb labeled with FITC-labeled secondary antibodies diluted in PBS for 1 hour at 22° C. After again washing four times with PBS for 5 minutes each, the samples were mounted in Mowiol mounting media (prepared as follows: 9 ml/glycerol and 3.36 g Mowiol 40-88 were agitated for 1 h at 22° C. Then, 9 ml of water was then added, and agitation continued for 2 h at 22° C. Tris (0.2 M, pH 8.5; 18 ml) was then added, and the solution incubated for 6 h at 50° C. until the solids were almost completely dissolved. After centrifugation at 5,000×g, the liquid phase was used for mounting), observed under a microscope, and photographed.

Figure 2:
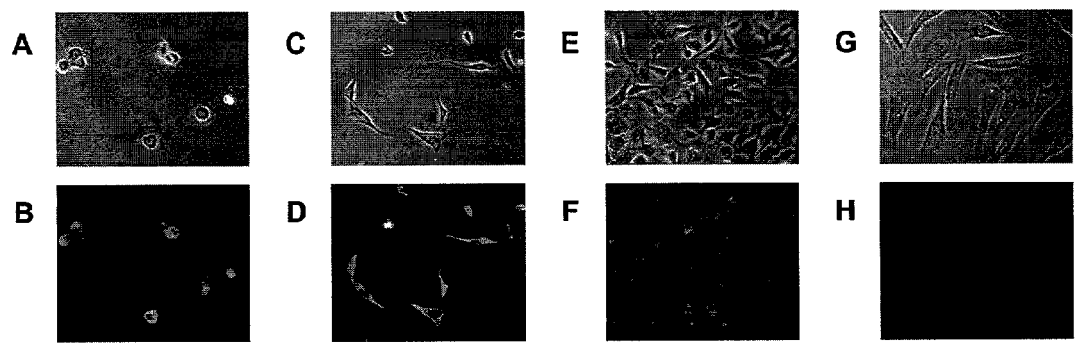
FIG. 2 shows plasma membrane nucleolin staining in the cell lines shown in FIG. 1. Shown are immunofluorescent (B, D, F, H) and parallel phase contrast micrographs (A, C, E, G). Cell lines that were analyzed were: DU145 prostate cancer cells (A, B), MDA-MB-231 breast cancer cells (C, D), HeLa cervical cancer cells (E, F) and HS27 normal skin cells (G, H). An anti-nucleolin antibody was used; the cells were not permeabilized before staining, allowing the antibody access to only the plasma membrane.

FIGS. 1 and 2 show nuclear (FIG. 1) and plasma membrane (FIG. 2) nucleolin staining in the various cell lines. Shown are immunofluorescent (FIGS. 1 and 2; panels B, D, F, H) and parallel phase contrast micrographs (FIGS. 1 and 2; panels A, C, E, G); DU145 cells are shown in A and B; MDA-MB-231 cells are shown in C and D; HeLa cells are shown in E and F; and HS27 cells are shown in G and H. All cell lines show clear nuclear nucleolin staining (FIGS. 1A, 1C, 1E and 1G). Note that when the cells are not permeabilized, thus restricting antibody access to the surface plasma membrane, the normal skin cell line, HS27, is completely negative for plasma membrane staining (FIG. 2H) while cancer cells show strong staining (FIGS. 2B, 2D, 2F and 2H). Staining plasma membrane nucleolin is thus a superior method for diagnosis and prognosis compared to nuclear nucleolin or silver-staining NORs.

Example 2

Correlation of the Degree of Plasma Membrane Nucleolin Expression and Cancer Aggressiveness This experiment demonstrates that cell lines with high levels of plasma membrane nucleolin correspond to those with the most rapid proliferation.

Two cancer cell lines, DU145 and HeLa, and one normal cell line, HS27, were assayed for proliferation rate and compared. Cell doubling time is calculated by determining cell density at regular intervals using the MTT assay (based upon the ability of living cells to reduce 3-(van de Loosdrecht et al., 1994)-2,5 diphenyltetrazolium bromide (MTT) into formazan; (van de Loosdrecht et al., 1994)), and confirmed by counting the cells using trypan blue exclusion.

Figure 3:
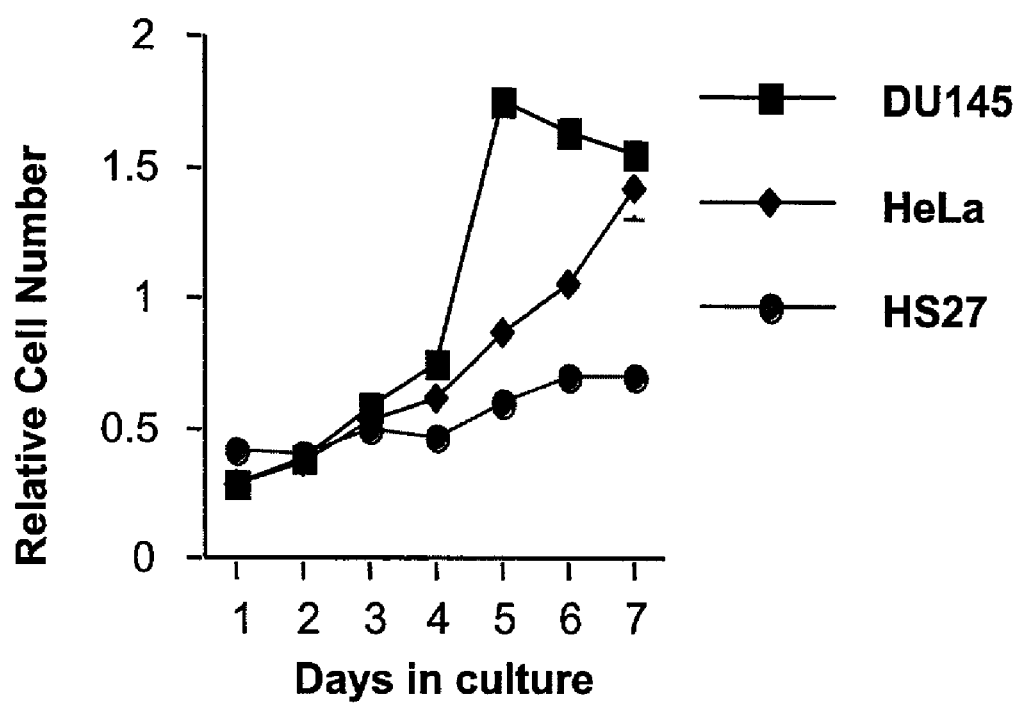
FIG. 3 shows the comparative proliferation rates of cell lines as measured by MTT assay. Square, DU145; diamonds, HeLa; circles, HS27. Although MDA-MB-231 was not included in this experiment, proliferation rates for these four cell lines have been determined to be DU145>MDA-MB-231>HeLa>HS27. Note that the cell lines with high levels of plasma membrane nucleolin correspond to those with the most rapid proliferation (DU145 and HeLa; see FIG. 2).

FIG. 3 shows the comparative proliferation rates of DU145 (squares), HeLa (diamonds) and HS27 (circles) as measured by MTT assay. Until 3 days of culture, growth rates are similar, but after 3 days, HeLa and DU145 increase at a faster rate than the normal HS27 cells. Although MDA-MB-231 was not included in this experiment, proliferation rate has been determined to be DU145>MDA-MB-231>HeLa>HS27. Note that the cell lines with high levels of plasma membrane nucleolin (see FIG. 2) correspond to those with the most rapid proliferation (DU145 and HeLa).

Example 3

Immunofluorescent Labeling of Nucleolin in Paraffin-Embedded Tissue Sections

This example provides a suitable technique to detect and localize nucleolin in a fixed sample that has been embedded.

Sections of cells fixed and embedded in paraffin wax and anchored on microscope slides were washed in three changes of xylene (2 minutes each) to remove the paraffin, hydrated in graded alcohols (series 100%, 95% and 70%; 2 minutes each), and placed in PBS for 5 minutes. Antigen recovery used the approach of low temperature antigen retrieval (LTAR; (Shi et al., 1997; Shi et al., 2001)): After digestion with 0.1% trypsin-EDTA (v/v)(Invitrogen Corp.; Carlsbad, Calif.) diluted in PBS for 15 minutes at 37° C./5% $CO_2$, the samples were washed with deionized water and incubated in 10 mM citrate buffer (pH 6) for 2 hours at 80° C. After cooling, the slides were rinsed with deionized water and then PBS.

Non-specific binding sites were blocked by incubation in 3% BSA in PBS for 30 minutes at 22° C. The samples were then incubated with 4 µg/ml mouse anti-nucleolin mAb (Santa Cruz) diluted in PBS/1% NGS at 4° C. overnight. The samples were then brought to 22° C., washed four times with PBS for 5 minutes, and then reacted with 50 µg/ml Alexa488-conjugated goat anti-mouse IgG (Molecular Probes; Eugene, Oreg.) and 2 µg/ml propidium iodide diluted in PBS/1% NGS for 1 hour at 22° C. After washing four times with PBS for 5 minutes, the samples were mounted in Mowiol mounting medium and observed under a fluorescent microscope.

Figure 4:
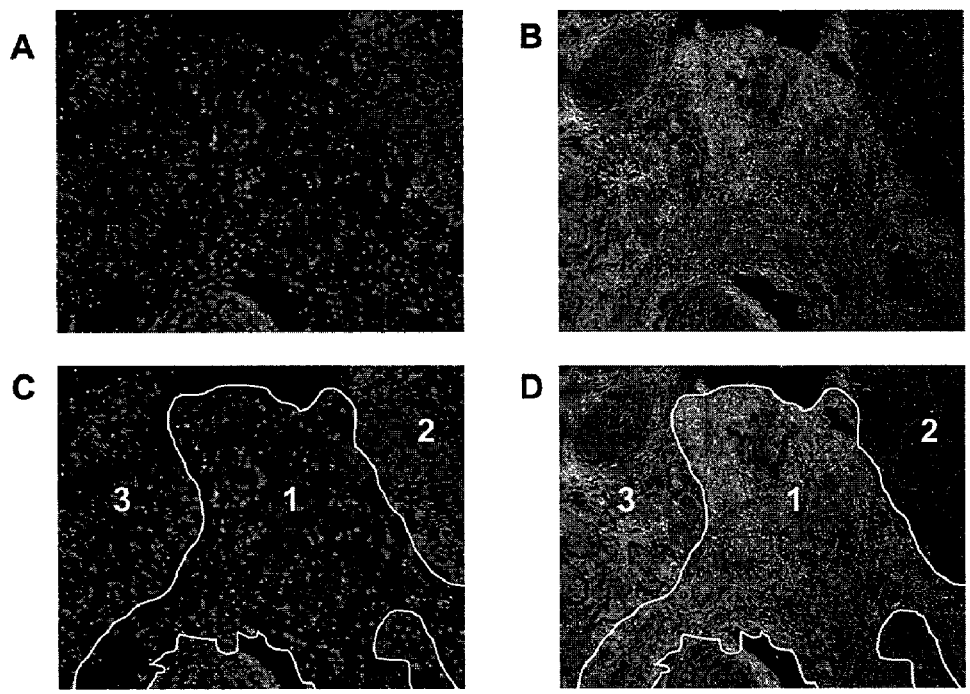
FIG. 4 shows phase contrast (B, D) and immunofluorescent image (A, C) of a paraffin-embedded specimen resected from a patient with squamous cell carcinoma of the head and neck. The specimen was stained for plasma membrane nucleolin and counter-stained with propidium iodide to show cell nuclei. Images (C) and (D) show images (A) and (B) overlaid with markings to better show nucleolin staining. The area 1 encompassed by the white line includes intense nucleolin staining, while the areas outside of 1 show little 3 or no 2 signal.

FIG. 4 shows the results of such an experiment. A clinical sample of a squamous cell carcinoma of the head and neck was prepared and probed for plasma membrane nucleolin. Plasma membrane nucleolin signal was relegated to malignant, neoplastic cells. FIG. 4A shows the immunofluorescent signal obtained from probing for nucleolin; the nuclei are counterstained with a DNA-intercalating dye. FIG. 4B shows a parallel phase contrast micrograph. FIGS. 4C and 4D are duplicates of FIGS. 4A and 4B, except markings have been added to better indicate areas of staining. In region 1, the signal is strong on the cells (faint signal in relation to the nuclear staining in FIG. 4A); these cells are in loosely-organized tissue and are less densely-packed, suggesting that they are malignant. In region 2, normal cells (as delineated by well-packed cells and organized tissue), cells display no plasma membrane nucleolin signal.

Example 4

Plasma Membrane Nucleolin Expression in Lung Carcinoma Cells

This example demonstrates that lung carcinoma cells can be easily identified by staining for plasma membrane nucleolin.

NCI-H1299 (non-small cell lung carcinoma isolated from *H. sapiens* lymph node; (Giaccone et al., 1992; Lin and Chang, 1996)) and NCI-H82 (small cell lung carcinoma cells, *H. sapiens*, (Carney et al., 1985; Little et al., 1983; Takahashi et al., 1989)) cells were released from culture substrates with trypsin, resuspended into single cells and plated onto microscope slides. The cells were incubated at 37° C. until they were well-attached as assayed by visual inspection using a microscope. After rinsing the cells once with PBS for 2 minutes, they were fixed in 4% formaldehyde/PBS for at least 15 minutes at 22° C. After washing twice with PBS, 5 minutes/wash, non-specific binding sites were blocked for 15-60 minutes with 1% NGS/PBS at 22° C., and then incubated with mouse anti-nucleolin antibodies for 1 hour to overnight at 4° C. The samples were washed four times, 5 minutes each with PBS and then incubated with goat anti-mouse pAb labeled with FITC-labeled secondary antibodies diluted in PBS with propidium iodide (to stain nuclei) for 1 hour at 22° C. After again washing four times with PBS for 5 minutes each, the samples were mounted in Mowiol mounting media, observed under a microscope and photographed.

Figure 5:
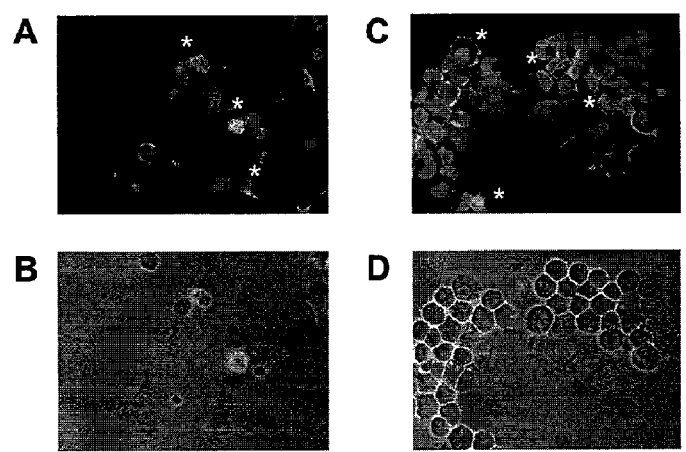
FIG. 5 shows phase contrast (B, D) and immunofluorescent images (A, C) of small cell (NCI-H82) and non-small cell lung (NCI-H1299) cancer cell lines placed onto a microscope slide using a cytospinner. Samples were stained for plasma membrane nucleolin and counter-stained with propidium iodide to show cell nuclei. Cells with exceptionally well-stained plasma membranes are denoted by asterisks (*).

FIG. 5 shows whole cells probed for plasma membrane nucleolin of the two lung cancer cell lines, NCI-H82 (FIG. 5A; a parallel phase contrast image is shown in 5B) and NCI-H1299 (FIG. 5C; a parallel phase contrast image is shown in 5D).

In both cell lines, plasma membrane nucleolin staining is strong; examples of well-stained cells are denoted by asterisk (*) in FIGS. 5A and 5C.

Example 5

Plasma Membrane Nucleolin Staining of Clinical Specimens

Figure 6:
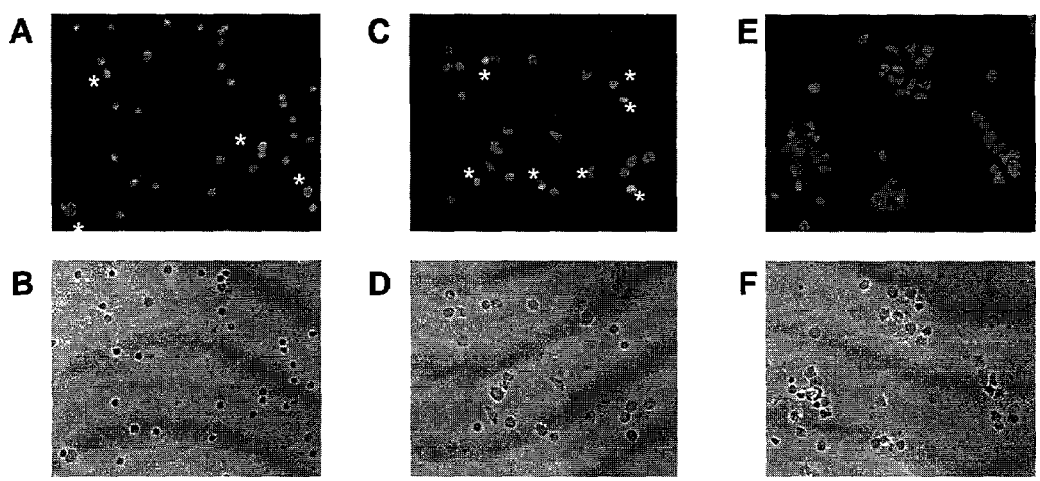
FIG. 6 shows phase contrast (B, D, F) and immunofluorescent images (A, C, E) of peripheral blood (A, B) or bone marrow (C, D and E, F) from human subjects. Samples were stained for plasma membrane nucleolin and counter-stained with propidium iodide to show cell nuclei. Highly stained cells for nucleolin are marked with an asterisk (*); these were only seen in those patients suffering from carcinomas (A,B and C,D), while cells from a healthy patient did not display any plasma membrane nucleolin staining (E, F).

To test the feasibility of using this novel method of assaying plasma membrane nucleolin to diagnose tumor, pre-malignant and malignant cells, clinical specimens from healthy subjects and those suffering from a cancer were collected. Samples from peripheral blood, bone marrow and tumor biopsy samples were obtained and stained for plasma membrane nucleolin as described in Example 4. FIG. 6 shows phase contrast (B, D, F) and immunofluorescent images (A, C, E) of peripheral blood (A, B) or bone marrow (C, D and E, F). Highly stained cells for plasma membrane nucleolin are marked with an asterisk (*); these were only seen in those patients suffering from carcinomas (A,B and C,D), while cells from a healthy patient did not display any plasma membrane staining (E, F).

Example 6

(Prophetic) Correlation of the Degree of Plasma Membrane Nucleolin Expression and Cancer Aggressiveness Thirty-three lung carcinoma cell lines are analyzed, mostly available from the American Type Culture Collection (Manassas, Va.). Cell doubling time is calculated by determining cell density at regular intervals using the MTT assay and confirmed by counting the cells using trypan blue exclusion. In each experiment HeLa cells (Gey et al., 1952) are included as an internal control. Each value is determined from at least two independent experiments with triplicate samples. To determine levels of nuclear and plasma membrane nucleolin, two methods are implemented. First, nuclear and plasma membrane extracts are prepared from each cell line using methods that have as described (Ausubel et al., 1987; Bates et al., 1999; Yao et al., 1996a). Briefly, cells are harvested and resuspended in a hypotonic buffer, then allowed to swell on ice for several minutes. Cells are lysed using a Dounce homogenizer, and nuclei are collected by centrifugation. Nuclei are resuspended in a high salt buffer to extract nuclear proteins; salt is then removed by dialysis. Plasma membrane proteins can be isolated from the S-100 fraction and are separated from cytosolic proteins and other organelles by centrifugation through a sucrose gradient. Nuclear and PM extracts from different cell are analyzed by Western blot analysis (Ausubel et al., 1987) using an anti-nucleolin antidody (Santa Cruz) followed by chemiluminescent visualization. Nucleolin levels are then quantified by densitometry of the resulting signal recorded on X-ray film and normalized to the intensity of HeLa extract controls. The second approach to determine nucleolin levels involves immunofluorescent probing of the cell lines for nucleolin. Cells are probed for nucleolin surface expression in parallel with DU145 cells (Mickey et al., 1977; Stone et al., 1978) as a positive control, HS27 cells as a negative control and HeLa cells as a reference (see FIG. 2). Cells are photographed and ranked in order of degree of signal, which may also be quantified (using systems that use software and images to quantitate pixels; in this instance, video images are used)or qualitatively evaluated. The data are then subjected to statistical analysis to demonstrate correlations with the degree of cell proliferation (higher rates of cell proliferation indicate more aggressive cancer cells) with the intensity of nucleolin signal across the entire sample and within subsets.

Example 7

(Prophetic) Lung Cancer Detection

In this example, patient biopsies, sputum samples and resected lung tissue are probed for plasma membrane nucleolin, and these results are compared to other diagnostic and prognostic markers for lung cancer, utilizing archival and routine clinical specimens for this study.

Methods

Specimens including bronchial biopsies, sputum samples, and resected lung tissue are obtained from human subjects, both healthy and those suffering from lung cancer, and each sample encoded such that at the time of nucleolin probing and observation, the sample origin is unknown.

Probing these samples using immunohistochemical techniques are then implemented. For example, plasma membrane nucleolin is probed with one or more anti-nucleolin Abs selected from Table 1, a signal generated from a flourophore-tagged secondary Ab, and the samples observed and photographed. Appropriate controls include probing with the secondary antibody only, probing with no antibodies, probing with pre-immune serum only, and probing with an antibody known not to react with the cell types being analyzed. To facilitate visualization and localization determination, the cells can be counterstained with Hoechst 33258 or propidium iodide (to visualize nuclei) and/or with fluorescent-tagged phalloidin or phallicidin (to visualize the actin cytoskeleton). The samples are observed, scored (surface signal indicating plasma membrane nucleolin expression) and documented.

REFERENCES

Ausubel, F. M., R. Brent, R. E. Kingston, D. D. Moore, et al. 1987. Current protocols in molecular biology. John Wiley & Sons, New York.

Babkes, M., A. Ranford, and K. Yaeger. U.S. Pat. No. 6,325, 785. 2001. Sputum trap manifold with nested caps.

Bandman, O., H. Yue, N. Corley, and P. Shah. U.S. Pat. No. 5,932,475. 1999. Human nucleolin-like protein.

Bates, P. J., J. B. Kahlon, S. D. Thomas, J. O. Trent, et al. 1999. Antiproliferative activity of G-rich oligonucleotides correlates with protein binding. *J Biol Chem.* 274:26369-77.

Byrne, C. J. 1986. Laboratory tests: implications for nursing care. Addison-Wesley Pub. Co. Health Sciences Division, Menlo Park, Calif. xxi, 756 pp.

Callebaut, C., J. Blanco, N. Benkirane, B. Krust, et al. 1998. Identification of V3 loop-binding proteins as potential receptors implicated in the binding of HIV particles to CD4(+) cells. *J Biol Chem.* 273:21988-97.

Carney, D. N., A. F. Gazdar, G. Bepler, J. G. Guccion, et al. 1985. Establishment and identification of small cell lung cancer cell lines having classic and variant features. Cancer Res. 45:2913-23.

Davis, K. A., Y. Lin, B. Abrams, and S. D. Jayasena. 1998. Staining of cell surface human CD4 with 2'-F-pyrimidine-containing RNA aptamers for flow cytometry. *Nucleic Acids Res.* 26:3915-24.

Derenzini, M. 2000. The AgNORs. *Micron.* 31:117-20.

Gey, G., W. Coffman, and M. Kubicek. 1952. Tissue culture studies of the proliferative capacity of cervical carcinoma and normal epithelium. *Cancer Res.* 12:264.

Giaccone, G., J. Battey, A. F. Gazdar, H. Oie, et al. 1992. Neuromedin B is present in lung cancer cell lines. *Cancer Res.* 52:2732s-2736s.

Ginisty, H., H. Sicard, B. Roger, and P. Bouvet. 1999. Structure and functions of nucleolin. *J Cell Sci.* 112:761-72.

Goding, J. W. 1996. Monoclonal antibodies: Principles and Practice. Academic Press, San Diego. 492 pp.

Harlow, E., and D. Lane. 1988. Antibodies: A laboratory manual. Cold Spring Harbor Laboratory Press, Cold Spring Harbor. 726 pp.

Harlow, E., and D. Lane. 1999. Using antibodies: A laboratory manual. Cold Spring Harbor Laboratory Press, Cold Spring Harbor, N.Y.

Kim, C. S., B. B. Berkley, W. M. Abraham, and A. Wanner. 1982. A micro double capillary method for rheologic measurements of lower airway secretions. *Bull Eur Physiopathol Respir.* 18:915-27.

King, M., and D. Speert. U.S. Pat. No. 6,339,075. 2002. Use of dextran and other polysaccharides to improve mucus clearance.

Langer, P. R., A. A. Waldrop, and D. C. Ward. 1981. Enzymatic synthesis of biotin-labeled polynucleotides: novel nucleic acid affinity probes. *Proc Natl Acad Sci USA.* 78:6633-7.

Lin, D. L., and C. Chang. 1996. p53 is a mediator for radiation-repressed human TR2 orphan receptor expression in MCF-7 cells, a new pathway from tumor suppressor to member of the steroid receptor superfamily. *J Biol Chem.* 271:14649-52.

Little, C. D., M. M. Nau, D. N. Carney, A. F. Gazdar, et al. 1983. Amplification and expression of the c-myc oncogene in human lung cancer cell lines. *Nature.* 306:194-6.

McNicol, A. M., and J. A. Richmond. 1998. Optimizing immunohistochemistry: antigen retrieval and signal amplification. *Histopathology.* 32:97-103.

Mickey, D. D., K. R. Stone, H. Wunderli, G. H. Mickey, et al. 1977. Heterotransplantation of a human prostatic adenocarcinoma cell line in nude mice. *Cancer Res.* 37:4049-58.

Miller, D., P. Bates, and J. Trent. WO 00/61597. 2000. Antiproliferative activity of G-rich oligonucleotides and method of using same to bind to nucleolin.

Naito, M., H. Hamada, and T. Tsuruo. 1988. ATP/$Mg^{2+}$-dependent binding of vincristine to the plasma membrane of multidrug-resistant K562 cells. *J. Biol Chem.* 263:11887-91.

Orfao, A., and A. Ruiz-Arguelles. 1996. General concepts about cell sorting techniques. *Clin Biochem.* 29:5-9.

Robinson, J. M., and D. D. Vandre. 2001. Antigen retrieval in cells and tissues: enhancement with sodium dodecyl sulfate. *Histochem Cell Biol.* 116:119-30.

Rubin, B., and M. Newhouse. U.S. Pat. No. 5,925,334. 1999. Use of surface active agents to promote mucus clearance.

Shi, S. R., R. J. Cote, and C. R. Taylor. 1997. Antigen retrieval immunohistochemistry: past, present, and future. *J Histochem Cytochem.* 45:327-43.

Shi, S. R., R. J. Cote, and C. R. Taylor. 2001. Antigen retrieval techniques: current perspectives. *J Histochem Cytochem.* 49:931-7.

Sorokina, E. A., and J. G. Kleinman. 1999. Cloning and preliminary characterization of a calcium-binding protein closely related to nucleolin on the apical surface of inner medullary collecting duct cells. *J Biol Chem.* 274:27491-6.

Srivastava, M., and H. B. Pollard. 1999. Molecular dissection of nucleolin's role in growth and cell proliferation: new insights. *Faseb J.* 13:1911-22.

Stone, K. R., D. D. Mickey, H. Wunderli, G. H. Mickey, et al. 1978. Isolation of a human prostate carcinoma cell line (DU 145). *Int J Cancer.* 21:274-81.

Takahashi, T., M. M. Nau, I. Chiba, M. J. Birrer, et al. 1989. p53: a frequent target for genetic abnormalities in lung cancer. *Science.* 246:491-4.

Tockman, M. S., J. L. Mulshine, S. Piantadosi, Y. S. Erozan, et al. 1997. Prospective detection of preclinical lung cancer: results from two studies of heterogeneous nuclear ribonucleoprotein A2/B1 overexpression. *Clin Cancer Res.* 3:2237-46.

Tuteja, R., and N. Tuteja. 1998. Nucleolin: a multifunctional major nucleolar phosphoprotein. *Crit Rev Biochem Mol. Biol.* 33:407-36.

van de Loosdrecht, A. A., R. H. Beelen, G. J. Ossenkoppele, M. G. Broekhoven, et al. 1994. A tetrazolium-based calorimetric MTT assay to quantitate human monocyte mediated cytotoxicity against leukemic cells from cell lines and patients with acute myeloid leukemia. *J Immunol Methods.* 174:311-20.

Wysocki, L. J., and V. L. Sato. 1978. "Panning" for lymphocytes: a method for cell selection. *Proc Natl Acad Sci USA.* 75:2844-8.

Xu, X., F. Hamhouyia, S. D. Thomas, T. J. Burke, et al. 2001. Inhibition of DNA Replication and Induction of S Phase Cell Cycle Arrest by G-rich Oligonucleotides. *J Biol Chem.* 276:43221-30.

Yao, G. Q., S. Corrias, and Y. C. Cheng. 1996a. Identification of two oligodeoxyribonucleotide binding proteins on plasma membranes of human cell lines. *Biochem Pharmacol.* 51:431-6.

Yao, G. Q., S. Corrias, and Y. C. Cheng. 1996b. Identification of two oligodeoxyribonucleotide binding proteins on plasma membranes of human cell lines. *Biochem Pharmacol.* 51:431-6.

---

The invention claimed is:

1. A method of determining presence of a malignant cell in a sample directly from a patient, comprising:
   obtaining a sample comprising a primary cell of the patient; and
   detecting the presence of plasma membrane nucleolin in the primary cell in the sample, to determine presence of the malignant cell.

2. The method of claim 1, wherein the primary cell is mammalian.

3. The method of claim 2, wherein the primary cell is monkey, dog, cat, rabbit, cow, pig, goat, guinea pig, mouse, rat or sheep.

4. The method of claim 2, wherein the primary cell is human.

5. The method of claim 1, wherein the primary cell is lysed.

6. The method of claim 1 wherein the detecting comprises detecting nucleolin-anti-nucleolin agent complex.

7. The method of claim 6, wherein the anti-nucleolin agent is a monoclonal antibody that specifically binds nucleolin.

8. The method of claim 7, wherein the antibody is p7-1A4 mouse monoclonal antibody, sc-8031, sc-9893, sc-9892, 4E2 or 3G4B2.

9. The method of claim 6, wherein the complex is detected by detecting fluorescence, an enzyme, or radioactivity.

10. A method of determining presence of a malignant cell in a sample directly from a patient, comprising:
    obtaining a sample comprising a primary cell of the patient; and
    quantifying the amount of plasma membrane nucleolin in a primary cell of the patient in the sample, to determine presence of the malignant cell.

11. The method of claim 10, wherein the primary cell is mammalian.

12. The method of claim 11, wherein the primary cell is monkey, dog, cat, rabbit, cow, pig, goat, guinea pig, mouse, rat or sheep.

13. The method of claim 12, wherein the primary cell is human.

14. The method of claim 10, wherein the primary cell is lysed.

15. The method of claim 10 wherein the quantifying comprises quantifying nucleolin-anti-nucleolin agent complex.

16. The method of claim 15, wherein the anti-nucleolin agent is a monoclonal antibody.

17. The method of claim 15, wherein the antibody is p7-1A4 mouse monoclonal antibody, sc-8031, sc-9893, sc-9892, 4E2 or 3G4B2.

18. The method of claim 1, wherein the primary cell is a lung cell.

19. The method of claim 1, wherein the sample comprises sputum.

20. The method of claim 1, further comprising, prior to the detecting: sending the sample to a testing center.

21. The method of claim 10, wherein the primary cell is a lung cell.

22. The method of claim 10, wherein the sample comprises sputum.

23. The method of claim 10, further comprising, prior to the quantifying:
collecting the sample directly from the patient; and
sending the sample to a testing center.

24. A method of determining presence of a malignant cell in a sample directly from a patient, comprising:
obtaining a sample comprising a primary cell of the patient; and
detecting the presence of plasma membrane nucleolin in the primary cell in the sample, to determine presence of the malignant cell;
wherein the detecting of the presence of plasma membrane nucleolin comprises:
contacting the primary cell with an antibody that specifically binds nucleolin; and
detecting the antibody bound to nucleolin, to detect the presence of plasma membrane nucleolin in the primary cell.

25. The method of claim 24, wherein the detecting of the presence of plasma membrane nucleolin comprises quantifying the amount of plasma membrane nucleolin in the primary cell.

26. The method of claim 25, wherein the primary cell is human.

27. The method of claim 26, wherein the antibody is a monoclonal antibody.

28. The method of claim 27, wherein the antibody is p7-1A4 mouse monoclonal antibody, sc-8031, sc-9893, sc-9892, 4E2 or 3G4B2.

29. The method of claim 26, wherein the detecting of the antibody bound to nucleolin comprises detecting fluorescence.

30. The method of claim 26, wherein the primary cell is a lung cell.

31. The method of claim 26, wherein the sample comprises sputum.

32. The method of claim 26, further comprising, prior to the detecting of the presence of plasma membrane nucleolin:
sending the sample to a testing center.

33. The method of claim 32, wherein the primary cell is a lung cell, and the sample comprises sputum.

34. A method of determining if a patient has cancer, comprising:
obtaining a sample comprising a primary cell of the patient;
detecting the presence of plasma membrane nucleolin in the primary cell in the sample; and
diagnosing the patient as having cancer.

* * * * *

UNITED STATES PATENT AND TRADEMARK OFFICE
CERTIFICATE OF CORRECTION

PATENT NO.       : 7,541,150 B2
APPLICATION NO.  : 10/118854
DATED            : June 2, 2009
INVENTOR(S)      : Donald M. Miller It is certified that error appears in the above-identified patent and that said Letters Patent is hereby corrected as shown below:

On the Title Page, under Foreign Patent Documents:

Col. 2, line 10, please delete "WO 02/44231" and insert --WO 02/44321--.

Title, item [56] Other Publications:

Page 2

Col. 1, line 58, please delete "Biochern" and insert --Biochem--.
Col. 1, lines 59-60, please delete "Traffocking" and insert --Trafficking--.
Col. 2, lines 40-41, please delete "Traffocking" and insert --Trafficking--.

Page 6

Col. 2, line 71, please delete "relateswith" and insert --relates with--.

Page 7

Col. 2, line 46, please delete the second "and".
Col. 2, line 69, please delete "juman" and insert --human--.

Page 8

Col. 1, line 42, please delete "p52" and insert --p53--.
Col. 2, line 12, please delete "os" and insert --of--.

UNITED STATES PATENT AND TRADEMARK OFFICE
CERTIFICATE OF CORRECTION

PATENT NO. : 7,541,150 B2
APPLICATION NO. : 10/118854
DATED : June 2, 2009
INVENTOR(S) : Donald M. Miller It is certified that error appears in the above-identified patent and that said Letters Patent is hereby corrected as shown below:

Column 1, under Federally Sponsored Research or Development line 5

Please delete "The U.S. Government may have rights in this invention." and insert --The U.S. Government has certain rights in this invention.--.

Signed and Sealed this

Twenty-eighth Day of July, 2009

JOHN DOLL
*Acting Director of the United States Patent and Trademark Office*

SEQUENCE LISTING

```
<160> NUMBER OF SEQ ID NOS: 38

<210> SEQ ID NO 1
<211> LENGTH: 29
<212> TYPE: DNA
<213> ORGANISM: Artificial sequence
<220> FEATURE:
<223> OTHER INFORMATION: synthetic oligonucleotide

<400> SEQUENCE: 1
tttggtggtg gtggttgtgg tggtggtgg                              29

<210> SEQ ID NO 2
<211> LENGTH: 29
<212> TYPE: DNA
<213> ORGANISM: Artificial sequence
<220> FEATURE:
```

-continued

```
<223> OTHER INFORMATION: synthetic oligonucleotide

<400> SEQUENCE: 2
tttggtggtg gtggttttgg tggtggtgg                                29

<210> SEQ ID NO 3
<211> LENGTH: 29
<212> TYPE: DNA
<213> ORGANISM: Artificial sequence
<220> FEATURE:
<223> OTHER INFORMATION: synthetic oligonucleotide

<400> SEQUENCE: 3
tttggtggtg gtggtggtgg tggtggtgg                                29

<210> SEQ ID NO 4
<211> LENGTH: 29
<212> TYPE: DNA
<213> ORGANISM: Artificial sequence
<220> FEATURE:
<223> OTHER INFORMATION: synthetic oligonucleotide

<400> SEQUENCE: 4
tttggtggtg gtggtttggg tggtggtgg                                29

<210> SEQ ID NO 5
<211> LENGTH: 13
<212> TYPE: DNA
<213> ORGANISM: Artificial sequence
<220> FEATURE:
<223> OTHER INFORMATION: synthetic oligonucleotide

<400> SEQUENCE: 5
tggtggtggt ggt                                                 13

<210> SEQ ID NO 6
<211> LENGTH: 14
<212> TYPE: DNA
<213> ORGANISM: Artificial sequence
<220> FEATURE:
<223> OTHER INFORMATION: synthetic oligonucleotide

<400> SEQUENCE: 6
ggtggttgtg gtgg                                                14

<210> SEQ ID NO 7
<211> LENGTH: 15
<212> TYPE: DNA
<213> ORGANISM: Artificial sequence
<220> FEATURE:
<223> OTHER INFORMATION: synthetic oligonucleotide

<400> SEQUENCE: 7
gttgtttggg tggt                                                15

<210> SEQ ID NO 8
<211> LENGTH: 15
<212> TYPE: DNA
<213> ORGANISM: Artificial sequence
<220> FEATURE:
<223> OTHER INFORMATION: synthetic oligonucleotide

<400> SEQUENCE: 8 ttggggggggg tgggt                                              15
```

<210> SEQ ID NO 9
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 9
ggttggggtg ggtggggtgg gtggg                                      25

<210> SEQ ID NO 10
<211> LENGTH: 26
<212> TYPE: DNA
<213> ORGANISM: Artificial sequence
<220> FEATURE:
<223> OTHER INFORMATION: synthetic oligonucleotide

<400> SEQUENCE: 10
ggtggtggtg gttgtggtgg tggtgg                                     26

<210> SEQ ID NO 11
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 11
tttggtggtg gtggttgtgg tggtggtg                                   28

<210> SEQ ID NO 12
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 12
tttggtggtg gtggtgtggt ggtggtgg                                   28

<210> SEQ ID NO 13
<211> LENGTH: 29
<212> TYPE: DNA
<213> ORGANISM: Artificial sequence
<220> FEATURE:
<223> OTHER INFORMATION: synthetic oligonucleotide

<400> SEQUENCE: 13
ggtggtggtg gttgtggtgg tggtggttt                                  29

<210> SEQ ID NO 14
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 14
ggtggttgtg gtggttgtgg tggttgtggt gg                              32

<210> SEQ ID NO 15
<211> LENGTH: 32
<212> TYPE: DNA
<213> ORGANISM: Artificial sequence
<220> FEATURE:
<223> OTHER INFORMATION: synthetic oligonucleotide

<400> SEQUENCE: 15
tttggtggtg gtggttgtgg tggtggtggt tt                          32

<210> SEQ ID NO 16
<211> LENGTH: 56
<212> TYPE: DNA
<213> ORGANISM: Artificial sequence
<220> FEATURE:
<223> OTHER INFORMATION: synthetic oligonucleotide

<400> SEQUENCE: 16
ggtggtggtg gttgtggtgg tggtggttgt ggtggtggtg gttgtggtgg tggtgg    56

<210> SEQ ID NO 17
<211> LENGTH: 35
<212> TYPE: DNA
<213> ORGANISM: Artificial sequence
<220> FEATURE:
<223> OTHER INFORMATION: synthetic oligonucleotide

<400> SEQUENCE: 17
tcgagaaaaa ctctcctctc cttccttcct ctcca                       35

<210> SEQ ID NO 18
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 18
tttcctcctc ctccttctcc tcctcctcc                              29

<210> SEQ ID NO 19
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 19
ttagggttag ggttagggtt aggg                                   24

<210> SEQ ID NO 20
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 20
ggtggtggtg g                                                 11

<210> SEQ ID NO 21
<211> LENGTH: 14
<212> TYPE: DNA
<213> ORGANISM: Artificial Sequence
<220> FEATURE:
<223> OTHER INFORMATION: synthetic oligonucleotide

<400> SEQUENCE: 21
ggtggttgtg gtgg                                              14

<210> SEQ ID NO 22
<211> LENGTH: 15

```
<212> TYPE: DNA
<213> ORGANISM: Artificial Sequence
<220> FEATURE:
<223> OTHER INFORMATION: synthetic oligonucleotide

<400> SEQUENCE: 22
ggttggtgtg gttgg                                                    15

<210> SEQ ID NO 23
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 23
gggttttggg                                                          10

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
ggttttggtt ttggttttgg                                               20

<210> SEQ ID NO 25
<211> LENGTH: 15
<212> TYPE: DNA
<213> ORGANISM: Artificial sequence
<220> FEATURE:
<223> OTHER INFORMATION: synthetic oligonucleotide

<400> SEQUENCE: 25
ggttggtgtg gttgg                                                    15

<210> SEQ ID NO 26
<211> LENGTH: 12
<212> TYPE: DNA
<213> ORGANISM: Artificial sequence
<220> FEATURE:
<223> OTHER INFORMATION: synthetic oligonucleotide

<400> SEQUENCE: 26
ggggttttgg gg                                                       12

<210> SEQ ID NO 27
<211> LENGTH: 10
<212> TYPE: DNA
<213> ORGANISM: Artificial sequence
<220> FEATURE:
<223> OTHER INFORMATION: synthetic oligonucleotide

<400> SEQUENCE: 27
gggttttggg                                                          10

<210> SEQ ID NO 28
<211> LENGTH: 28
<212> TYPE: DNA
<213> ORGANISM: Artificial sequence
<220> FEATURE:
<223> OTHER INFORMATION: synthetic oligonucleotide

<400> SEQUENCE: 28
```

| ggggttttgg ggttttgggg ttttgggg | 28 |

<210> SEQ ID NO 29
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 29

| ttggggttgg ggttggggtt gggg | 24 |

<210> SEQ ID NO 30
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 30

| gggtgggtgg gtgggt | 16 |

<210> SEQ ID NO 31
<211> LENGTH: 26
<212> TYPE: DNA
<213> ORGANISM: artificial sequence
<220> FEATURE:
<223> OTHER INFORMATION: synthetic oligonucleotide

<400> SEQUENCE: 31

| ggttttggtt ttggttttgg ttttgg | 26 |

<210> SEQ ID NO 32
<211> LENGTH: 29
<212> TYPE: DNA
<213> ORGANISM: artificial sequence
<220> FEATURE:
<223> OTHER INFORMATION: synthetic oligonucleotide

<400> SEQUENCE: 32

| tttcctcctc ctccttctcc tcctcctcc | 29 |

<210> SEQ ID NO 33
<211> LENGTH: 26
<212> TYPE: DNA
<213> ORGANISM: artificial sequence
<220> FEATURE:
<223> OTHER INFORMATION: synthetic oligonucleotide

<400> SEQUENCE: 33

| cctcctcctc cttctcctcc tcctcc | 26 |

<210> SEQ ID NO 34
<211> LENGTH: 6
<212> TYPE: DNA
<213> ORGANISM: artificial sequence
<220> FEATURE:
<223> OTHER INFORMATION: synthetic oligonucleotide

<400> SEQUENCE: 34

| tggggt | 6 |

<210> SEQ ID NO 35
<211> LENGTH: 7
<212> TYPE: DNA
<213> ORGANISM: artificial sequence -continued

```
<220> FEATURE:
<223> OTHER INFORMATION: synthetic oligonucleotide

<400> SEQUENCE: 35 gcatgct                                                                        7

<210> SEQ ID NO 36
<211> LENGTH: 11
<212> TYPE: DNA
<213> ORGANISM: Artificial sequence
<220> FEATURE:
<223> OTHER INFORMATION: synthetic oligonucleotide

<400> SEQUENCE: 36
gcggtttgcg g                                                                  11

<210> SEQ ID NO 37
<211> LENGTH: 4
<212> TYPE: DNA
<213> ORGANISM: artificial sequence
<220> FEATURE:
<223> OTHER INFORMATION: synthetic oligonucleotide

<400> SEQUENCE: 37 tagg                                                                           4

<210> SEQ ID NO 38
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 38
ggggttgggg tgtggggttg ggg                                                     23
```